US009315534B2

(12) United States Patent
Kortylewicz et al.

(10) Patent No.: US 9,315,534 B2
(45) Date of Patent: Apr. 19, 2016

(54) RADIOLOGIC AGENTS FOR MONITORING ALZHEIMER'S DISEASE PROGRESSION AND EVALUATING A RESPONSE TO THERAPY AND PROCESSES FOR THE PREPARATION OF SUCH AGENTS

(75) Inventors: Zbigniew P. Kortylewicz, Omaha, NE (US); Janina Baranowska-Kortylewicz, Omaha, NE (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 2114 days.

(21) Appl. No.: 12/188,641

(22) Filed: Aug. 8, 2008

(65) Prior Publication Data

US 2009/0117041 A1 May 7, 2009

Related U.S. Application Data

(60) Provisional application No. 60/964,251, filed on Aug. 10, 2007, provisional application No. 61/010,129, filed on Jan. 4, 2008.

(51) Int. Cl.
*A61K 51/00* (2006.01)
*A61M 36/14* (2006.01)
*C07H 19/073* (2006.01)
*A61K 51/04* (2006.01)

(52) U.S. Cl.
CPC .......... *C07H 19/073* (2013.01); *A61K 51/0459* (2013.01)

(58) Field of Classification Search
CPC .......................... C07H 19/073; A61K 51/0459
USPC ........................................................ 424/1.77
See application file for complete search history.

(56) References Cited

U.S. PATENT DOCUMENTS

| 7,270,800 B2 | 9/2007 | Klunk et al. |
| 2004/0138170 A1 | 7/2004 | Montgomery et al. |
| 2005/0069495 A1 | 3/2005 | Baranowska-Kortylewicz et al. |
| 2005/0136040 A1 | 6/2005 | Hart et al. |
| 2005/0222185 A1 | 10/2005 | Ahn et al. |
| 2009/0117041 A1 | 5/2009 | Kortylewicz et al. |

FOREIGN PATENT DOCUMENTS

WO 2006096757 A2 9/2006

OTHER PUBLICATIONS

Lorey et al. Nucleosides and Nucleotides, 1997, 789-792.*
C. Brown-Proctor et al., "Synthesis and Evaluation of 6-[11C]Methoxy-3-[2-[1-(phenylmethyl)-4-piperidinyl]ethyl]-1,2-benzisoxazole as an in Vivo Radioligand for Acetylcholinesterase", Nucl. Med. Biol., 26: 99-103 (1999).

M. I. Balagopala et al., "An Improved synthesis of Azidothymidine", Nucleosides & Nucleotides, 15(4): 899-906 (1996).
C. Altamirano et al., "The Butyrylcholinesterase K-Variant Shows Similar Cellular Protein Turnover and Quaternary Interaction to the Wild-Type Enzyme", J. Neurochemistry, 74: 869-77 (2000).
T. Arendt et al., "Changes in Acetylcholinesterase and Butyrylcholinesterase in Alzheimer's Disease Resemble Embryonic Development—a Study of Molecular Forms", Neurochem. Int., 21(3): 381-396 (1992).
M. Arpagaus et al., "Use of the Polymerase Chain Reaction for Homology Probing of Butyrylcholinesterase from Several Vertebrates", J. Biol. Chem., 266: 6966-74 (1991).
P. Arriagada et al., "Neurofibrillary tangles but not senile plaques parallel duration and severity of Alzheimer's disease", Neurology, 42: 631-639 (1992).
J. Atack et al., "Molecular Forms of Butyrylcholinesterase in the Human Neocortex During Development and Degeneration of the Cortical Cholinergic System", J. Neurochem., 48: 1687-92 (1987).
F. Atkinson et al., "Lipophilicity and Other Parameters Affecting Brain Penetration", Curr. Med. Chem., 2: 229-40 (2002).
M. Balagopala et al., "An Improved synthesis of Azidothymidine", Nucleosides & Nucleotides, 15(4): 899-906 (1996).
J. Baranowska-Kortylewicz et al., "Radiolabeling Kit/Generator for 5-Radiohalogenated Uridines", J. Labelled Compds. Radiopharm., 34: 513-512 (1994).
J. Bencherif et al., "PET Imaging of Brain Acetylcholinesterase Using [11C]CP-126,998, a Brain Selective Enzyme Inhibitor", Synapse, 45: 1-9 (2002).
J. Birks, "Cholinesterase inhibitors for Alzheimer's disease", Cochrane Database Syst. Rev., 1:CD0-005593 (2006).
R. Blesa et al., "Effect of butyrylcholinesterase genotype on the response to rivastigmine or donepezil in younger patients with Alzheimer's disease", Pharmacogenet. Genomics, 16: 771-4 (2006).
P. Buchwald et al., "Octanol-Water Partition: Searching for Predictive Models", Curr. Med. Chem., 5: 353-80 (1998).
R. Bullock et al., "Effect of age on response to rivastigmine or donepezil in patients with Alzheimer's disease", Curr. Med. Res. Opin., 22: 483-94 (2006).
J. Clement, "Pharmacological Nature of Soman-Induced Hypothermia in Mice", Phamacol. Biochem. Behav., 44: 689-702 (1993).
J. Coyle et al., "Alzheimer's Disease: A disorder of Cortical Cholinergic Innervation", Science, 219: 1184-1190 (1983).
G. Crisp, "Synthesis of 5-Alkenyl-2'-deoxyuridines via Organostannanes", Synthetic Comm., 19: 2117-23 (1989).
B. Cummings et al., "B-amyloid Deposition and Other Measures of Neuropathology Predict Cognitive Status in Alzheimer's Disease", Neurobiol. Aging, 17: 921-933 (1996).
F.O. Cunningham et al., "Encapsulated nerve endings in hairy skin", J. Anat., 112(1): 93-97 (1972).

(Continued)

*Primary Examiner* — Michael G Hartley
*Assistant Examiner* — Sean R Donohue
(74) *Attorney, Agent, or Firm* — Hovey Williams LLP

(57) ABSTRACT

Disclosed are certain cycloSalingenyl pyrimidine nucleoside monophosphates comprising positron emitters or gamma-emitting radiohalides, uses thereof for monitoring Alzheimer's disease progression and evaluating response to therapy and process for their preparation.

11 Claims, 10 Drawing Sheets

(56) References Cited

OTHER PUBLICATIONS

T. Darreh-Shori et al., "Differential CSF butyrylcholinesterase levels in Alzheimer's disease patients with the ApoE E4 allele, in relation to cognitive function and cerebral glucose metabolism", Neurobiol. Dis., 24: 326-33 (2006).

P. Davies et al., "Selective Loss of Central Cholinergic Neurons in Alzheimer's Disease", The Lancet, 2: 1403 (1976).

B. P. Doctor et al., "Complete amino acid sequence of fetal bovine serum acetylcholinesterase and its comparison in various regions with other cholinesterases", FEBS Letts, 266: 123-127 (1990).

S. Dutta et al., "Steady-state propofol brain:plasma and brain:blood partition coefficients and the effect-site equilibration paradox", Br., J. Anaesth., 81: 422-4 (1998).

M. Flirski et al., "Biochemical Markers and Risk Factors of Alzheimer's Disease", Current Alzheimer Research, 2: 47-64 (2005).

P. T. Francis et al., "The cholinergic hypothesis of Alzheimer's disease: a review of progress", J. Neurol. Neurosurg. Psychiatry., 66: 137-47 (1999).

M. Garcia-Alloza, "Characterization of amyloid deposition in the APPswe/PS1dE9 mouse model of Alzheimer disease", Neurobiol. Dis., 24: 516-524 (2006).

S. Gauthier et al., A large, naturalistic, community-based study of rivastigmine in mild-to-moderate AD: the EXTEND Study, Curr. Med., Res., Opin., 22: 2251-65 (2006).

C. Geula et al., Butyrylcholinesterase, Cholinergic Neurotransmission and the Pathology of Alzheimer's Disease, Drugs Today (Barc)., 40: 711-21 (2004).

E. Ghebremedhin et al., "Homozygosity for the K variant of BCHE gene increases the risk for development of neurofibrillary pathology but not amyloid deposits at young ages", Acta Neuropathol., 114: 359-63 (2007).

E. Giacobini, "Selective Inhibitors of Butyrylcholinesterase: a valid alternative for therapy of Alzheimer's disease?" Drugs Aging, 18: 891-8 (2001).

E. Giacobini et al., "Inhibition of acetyl- and butyryl-cholinesterase in the cerebrospinal fluid of patients with Alzheimer's disease by rivastigmine: correlation with cognitive benefit", J. Neural Transm, 109: 1053-65 (2002).

E. Giacobini, "Cholinergic function and Alzheimer's disease", Int. J. Geriatr. Psychiatry, 18: S1-S5 (2003).

C. Gordon, "Thermoregulation in Laboratory Mammals and Humans Exposed to Anticholinesterase Agents", Neurotoxicol. Teratol, 16: 427-453 (1994).

N. Greig et al., "Selective butyrylcholinesterase inhibition elevates brain acetylcholine, augments learning and lowers Alzheimer B-amyloid peptide in rodent", PNAS, 102(47): 17213-17218 (2005).

J. Grierson et al., "Comparative Uptake and Cell Cycle Measurements with [F-18]FLT vs. [H-3]Thymidine in Mammalian Tumor Cells", J. Nucl. Med., 39(5): 229P (1998).

J. Grierson et al., "Optimizing Labeling Substrate Structure for 3'-Deoxy-3'-[F-18]Fluoroethymidine: [F-18]FLT", J. Nucl. Med., 40(5): 83P (1999) [Abstract].

J. Grierson et al., "Radiosynthesis of 3'-Deoxy-3'-[19F]fluorothymidine: [18F]FLT for Imaging of Cellular Proliferation In Vivo", Nucl. Med. Biol., 27: 143-156 (2000).

A. Guillozet et al., "Butyrylcholinesterase in the Life Cycle of Amyloid Plaques", Ann. Neurol., 42: 909-18 (1997).

C. Hansch et al., "Hydrophobicity and Central Nervous System Agents: On the Principle of Minimal Hydrophobicity in Drug Design", J. Pharm. Sci., 76: 663-87 (1987).

K. Herholz et al., "In-vivo measurements of regional acetylcholine esterase activity in degenerative dementia: comparison with blood flow and glucose metabolism", J. Neural. Transm., 107(12): 1457-68 (2000).

T. Irie et al., "Brain Acetylcholinesterase Activity: Validation of a PET Tracer in a Rat Model of Alzheimer's Disease", J. Nucl. Med., 37: 649-655 (1996).

S. Irwin, "Comprehensive Observational Assessment: Ia. A Systematic, Quantitative Procedure for Assessing the Behavorial and Physiologic State of the Mouse", Psychopharmacologia (Berl.), 13: 222-257 (1968).

M. Iyo et al., Measurement of acetylcholinesterase by position emission tomography in the brains of healthy controls and patients with Alzheimer's disease, The Lancet, 349: 1805-1809 (1997).

J. Jankowsky et al., "Mutant presenilins specifically elevate the levels of the 42 residue B-amyloid peptide in vivo: evidence for augmentation of a 42-specific gamma secretase", Hum. Mol. Genet., 13: 159-70 (2004).

H. Jessen et al., "Synthesis and Properties of Fluorescent cycloSal Nucleotides Based on the Pyrimidine Nucleoside m5K and Its 2',3'-Dideoxy Analog dm5K", Eur. J. Org. Chem., 924-931 (2006).

K. Johnson, "Amyloid Imaging of Alzheimer's Disease Using Pittsburgh Compound B", Curr. Neurol. Neurosci. Rep., 6: 496-503 (2006).

R. Kuljis et al., "Tomographic Visualization of Cholinesterase", Ann. Neurol., 60(6): 745-6 (2006).

M. Kung et al., "IMPY: an improved thioflavin-T derivative for in vivo labeling of B-amyloid plaques", Brain Research, 956: 202-210 (2002).

M. Kung et al., "Development and Evaluation of Iodinated Tracers Targeting Amyloid Plaques for SPECT Imaging", J. Mol. Neurosci., 24: 49-53 (2004).

D. Lahiri et al., "A Critical Analysis of New Molecular Targets and Strategies for Drug Developments in Alzheimer's Disease", Current Drug Targets, 4: 97-112 (2003).

D. Lahiri et al., "Rationale for the Development of Cholinesterase Inhibitors as Anti-Alzheimer Agents", Curr. Pharm. Des., 10: 3111-9 (2004).

P. Layer et al., "Nonclassical Roles of Cholinesterases in the Embryonic Brain and Possible Links to Alzheimer Disease", Alzheimer Dis. Assoc. Disord., 9, Suppl. 2: 29-36 (1995).

S. Lopez-Pousa et al., "Differential Efficacy of Treatment with Acetylcholinesterase Inhibitors in Patients with Mild and Moderate Alzheimer's Disease over a 6-Month Period", Dement. Geriatr. Cogn. Disord., 19: 189-95 (2005).

H.J. Machulla et al., Simplified labeling approach for synthesizing 3'-deoxy-3'-[18F]fluorothymidine ([18F]FLT), J. Radioanal. Nucl. Chem., 243: 843-846 (2000).

S. J. Martin et al., "A new precursor for the radiosynthesis of [18F]FLT", Nucl. Med. Biol., 29: 263-273 (2002).

A. C. McKee et al., "Neuritic Pathology and Dementia in Alzheimer's Disease", Ann. Neurol., 30: 156-165 (1991).

H. McLoughlin et al., "Encapsulated nerve endings in murine dorsal ear skin", J. Anat., 167: 215-223 (1989).

M.R. Kilbourn et al., In Vivo Studies of Acetylcholinesterase Activity Using a Labeled Substrate, N-[11C] Methylpiperdin-4-yl Propionate ([11C]PMP), Synapse, 22: 123-131 (1996).

K.S. Kim et al., "Detection and Quantitation of Amyloid B-Peptide with 2 Monoclonal Antibodies", Neurosci. Res. Comm., 7: 113-122 (1990).

W. Klunk et al., "Imaging Brain Amyloid in Alzheimer's Disease with Pittsburgh Compound-B", Ann. Neurol., 55: 306-19 (2004).

D. S. Knopman et al., "Neuropathy of Cognitively Normal Elderly", J. Neuropathol. Exp. Neurol., 62: 1087-1095 (2003).

Z. Kovarik et al., "Acetylcholinesterase active centre and gorge conformations analysed by combinatorial mutations and enantiomeric phosphonates", Biochem. J., 373: 33-40 (2003).

D. Kuhl et al., "In Vivo Butyrylcholinesterase Activity is Not Increased in Alzheimer's Disease Synapses", Ann. Neurol., 59: 13-20 (2006).

C. Meier et al., "Nucleotide Delivery from cycloSaligenyl-3'-azido-3'-deoxythymidine Monophosphates (cycloSal-AZTMP)", Eur. J. Org. Chem., 837-846 (1998).

C. Meier et al., "cycloSal-Pronucleotides of 2'-Fluoro-ara- and 2'-Fluoro-ribo-2',3'-dideoxyadenosine as a Strategy to Bypass a Metabolic Blockade", J. Med.Chem., 42: 1615-1624 (1999).

C. Meier, "cycloSal-Pronucleotides-Design of Chemical Trojan Horses", Mini Rev. Med. Chem., 2: 2129-34 (2002).

(56) References Cited

OTHER PUBLICATIONS

C. Meier, "Interaction of cycloSal-Pronucleotides with Cholinesterases from Different Origins. A Structure-Activity Relationship", J. med. Chem., 47; 2839-2852 (2004).

J. Mercer et al., "Synthesis and Tumor uptake of 5- 82Br- and 5-131 I-Labeled 5-Halo-1-(2-fluoro-2-deoxy-B-D-ribofuranosyl) uracils", J. Med. Chem., 32: 1289-1294 (1989).

M.Mesulam et al., "Butyrylcholinesterase Reactivity Differentiates the Amyloid Plaques of Aging from Those of Dementia", Ann. Neurol., 36: 722-7 (1994).

B. Moon et al., "Preparation of 3'-deoxy-3'-[18F]fluorothymidine (I18F]FLT) in ionic liquid, [OTf]", J. Labelled Compd. Radiopharm., 43: 1211-1218 (2000).

M. Moran et al., "Colocalization of cholinesterases with B amyloid protein in aged and Alzheimer's brains", Acta Neuropathol., 85: 362-9 (1993).

S. Nagatsuka et al., "Kinetic Analysis of [11C]MP4A Using a High-Radioactivity Brain Region that Represents an Integrated Input Function for Measurement of Cerebral Acetylcholinesterase Activity Without Arterial Blood Sampling", J. Cerebral Blood Flow and Metabolism, 21: 1354-1366 (2001).

H. Namba et al., "Human cerebral acetylcholinesterase activity measured with positron emission tomography: procedure, normal values and effect of age", Eur. J. Nucl. Med., 26: 135-43 (1999).

E. K. Perry et al., "Changes in Brain Cholinesterases in Senile Dementia of Alzheimer Type", Neuropathol. Appl. Neurobiol., 4: 273-7 (1978).

R. Perry et al., "Histochemical Observations on Cholinesterase Activities in the Brains of Elderly Normal and Demented (Alzheimer-type) Patients", Age and Ageing, 9: 9-16 (1980).

R. Raschetti et al., "A cohort study of effectiveness of acetylcholinesterase inhibitors in Alzheimer's disease", Eur. J. Clin. Pharmacol, 61: 361-368 (2005).

B. Reed., "Opening a window on cerebral cholinergic function: PET imaging of acetylcholinesterase", Neurology, 52: 680-682 (1999).

R. Schliebs et al., "The significance of the cholinergic system in the brain during aging and in Alzheimer's disease", J. Neurol. Transm., 113: 1625-1644 (2006).

G. Sharma et al., "Zirconium (IV) Chloride Catalyzed New and Efficient Protocol for the Selective Cleavage of p-Methoxybenzyl Ethers", J. Org. Chem., 68: 4574-4575 (2003).

A. Shields et al., "Imaging proliferation in vivo with [F-18]FLT and positron emission tomography", Nature Medicine, 4(11): 1334-1336 (1998).

K. Shoghi-Jadid et al., "Localization of Neurofibrillary Tangles and Beta-Amyloid Plaques in the Brains of Living Patients with Alzheimer Disease", Am J. Geriatr. Psychiatry, 10: 24-35 (2002).

E. Sigurdsson et al., "Local and Distant Histopathological Effects of Unilateral Amyloid-B 25-35 Injections into the Amygdala of Young F344 Rats", Neurobiology of Aging, 17(6): 893-901 (1996).

G. Small et al., "PET of Brain Amyloid and tau in Mild Cognitive Impairment", N. Engl. J. Med., 355: 2652-63 (2006).

S. Snyder et al., "Radiolabeled Cholinesterase Substrates: In Vitro Methods for Determining Structure-Activity Relationships and Identification of a Positron Emission Tomography Radiopharmaceutical for In Vivo Measurement of Butyrylcholinesterase Activity", J. Cereb. Blood Flow Metab., 21: 132-43 (2001).

A. Tasker et al., "Butyrylcholineasterase: impact on symptoms and progression of cognitive impairment", Expert Rev. Neurother., 5: 101-6 (2005).

S. A. Teijeiro et al., "Lipophilic Character of Pyrimidinic Nucleoside Derivatives: Correlation Between Shake Flask, Chromatographic (RP-TLC and RP-HPLC) and Theoretical Methods", J. Liq. Chrom. & Rel. Technol., 23(6): 855-872 (2000).

S. Tobias et al., "Synthesis and Biological Studies of Novel Nucleoside Phosphoramidate Prodrugs", J. Med. Chem., 44: 4475-4480 (2001).

J. H. van Boom et al., "Use of Levulinic Acid in the Protection of Oligonucleotides via the Modified Phosphotriester Method: Synthesis of Decaribonucleotide U-A-U-A-U-A-U-A-U-A", Tetrahedron Letters, 52: 4875-4878 (1976).

Y. Wang et al., "Development of a PET/SPECT Agent for Amyloid Imaging in Alzheimer's Disease", J. Mol. Neurosci., 24: 55-62 (2004).

J. Wegiel et al., "Intraneuronal AB immunoreactivity is not a predictor of brain amyloi8dosis-b or neurofibrillary degeneration", Acta Neuropathol., 113: 389-402 (2007).

M. Weinstock et al., "Ladostigil, a novel multifunctional drug for the treatment of dementia co-morbid with depression", J. Neural. Transm. Suppl., 70: 443-6 (2006).

P. Wigerinck et al., Synthesis and Antiviral Activity of 5-Thien-2-yl-2'-deoxyuridine Analogues, J. Med. Chem., 36: 538-543 (1993).

D. G. Wilkinson et al., "A Multinational, Randomised, 12-Week, Comparative Study of Donepezil and Rivastigmine in Patients with Mild to Moderate Alzheimer's Disease", Int. J. Clin. Pract., 56: 441-6 (2002).

C. Wodarski et al., "Synthesis of 3'-Deoxy-3'-[18F]Fluoro-Thymidine with 2,3'-Anhydro-5'-O-(4,4'-Dimethoxytrityl)-Thymidine", J. Labelled Compd. Radiopharm., 43: 1211-1218 (2000).

M. Yun et al., "High radiochemical yield synthesis of 3'-deoxy-3'-[18F]fluorothymidine using (5'-O-dimethoxytrityl-2'-deoxy-3'-O-nosyl-B-D-threo pentofuranosyl)thymine and its 3-N-BOC-protected analogue as a labeling precursor", J. Nucl. Med. Biol., 30: 152-157 (2003).

J. Grierson et al., "An improved radiosynthesis of [18F]FLT", J. Labelled Comp. Radiopharm., 42(suppl): 5525-5526 (1999).

J. Grierson et al., "Development of a Radiosynthesis for 3'-[F-18]Fluoro-3'-Deoxynucleosides", J. Labelled Compd Radiopharm., 40: 60-62 (1997).

D.E. Kuhl et al., "Mapping Acetylcholinesterase in Human Brain Using PET and N-[C-11]Methylpiperidinyl Propionate (PMP)", J. Nucl. Med., 37(5): 21P (1996).

M. J. Karnovsky et al., "A 'Direct-coloring' Thiocholine Method for Cholinesterases", J. Histochem. Cytochem., 12: 219-21 (1964.

J.S. Rasey et al., "3'-deoxy-3'-[F-18]fluorothymidine (FLT) predicts changes in cell proliferation", J. Nucl. Med., 40(5): 25P (1999).

S.R. Choi et al., "Novel Iodinated Nucleoside as a Potential Tumor Imaging Agent", J. Nucl. Med., 41(5) Suppl.: 233P (2000).

\* cited by examiner

RADIOLOGIC AGENTS FOR MONITORING ALZHEIMER'S DISEASE PROGRESSION AND EVALUATING A RESPONSE TO THERAPY AND PROCESSES FOR THE PREPARATION OF SUCH AGENTS

CROSS-REFERENCE TO RELATED APPLICATIONS

The present application claims the benefit of U.S. Provisional Patent Applications Nos. 60/964,251, filed Aug. 10, 2007 and 61/010,129, filed Jan. 4, 2008, the entire disclosures of which are incorporated by reference herein.

STATEMENT REGARDING FEDERAL SPONSORED RESEARCH OR DEVELOPMENT

This invention was made with government support under Grant No. W81XWH-04-1-0463 awarded by the Department of Defense. The Government has certain rights in this invention.

FIELD OF THE INVENTION

The present invention relates to certain cycloSalingenyl pyrimidine nucleoside monophosphates comprising positron emitters or gamma-emitting radiohalides, to uses thereof for monitoring Alzheimer's disease progression and evaluating response to therapy and to process for their preparation.

BACKGROUND OF THE INVENTION

Alzheimer's disease (AD) is the most common cause of dementia affecting older people. An estimated 4.5 million Americans and nearly 28 million people globally, a number that is predicted to rise sharply as the world population continues to age, are afflicted with AD. The estimate of the worldwide costs for AD dementia care is approximately $248 billion.

The formation of extracellular insoluble amyloid plaques of the β-amyloid peptide (Aβ) is regarded as the central common factor for the pathogenesis of AD. However, the accumulation of amyloid deposits is also an ever-present event in the aging brain, whether demented or not. One factor that distinguishes plaques present in AD is their ability to produce neuritic degeneration and neurofibrillary tangles (McKee et al. (1991) Ann. Neurol., 30:156-165; Arriagada et al. (1992) Neurology, 42:631-639; Cummings et al. (1996) Neurobiol. Aging, 17:921-933; Knopman et al. (2003) J. Neuropathol. Exp. Neurol., 62:1087-1095). Moreover, while the neuritic process itself is not yet fully understood, the frequency of neuritic plaques in the cerebral cortex shows a strong relationship with the severity of dementia. Biochemical investigations also suggest that companion molecule(s) associated with amyloid plaques facilitate the transformation of these plaques to their degenerative form. One such companion molecule is butyrylcholinesterase (BChE) (Lahiri et al. (2004) Curr. Pharm. Des., 10:3111-9; Lahiri et al. (2003) Curr. Drug Targets, 4:97-112; Giacobini et al. (2002) J. Neural. Transm., 109:1053-65; Layer, P. G. (1995) Alzheimer Dis. Assoc. Disord., 9 Suppl 2:29-36; Perry et al. (1978) Neuropathol. Appl. Neurobiol., 4:273-7; Perry et al. (1980) Age Ageing., 9:9-16; Guillozet et al. (1997) Ann. Neurol., 42:909-18; Mesulam et al. (1994) Ann. Neurol., 36:722-7).

Several lines of evidence suggest that BChE, possibly through its own proteolytic activity or in association with heparin sulfate proteoglycans, plays a role in the aggregation and consolidation processes taking place at the early stages of the plaque formation. Mesulam et al. (Guillozet et al. (1997) Ann. Neurol., 42:909-18; Mesulam et al. (1994) Ann. Neurol., 36:722-7) and others (Moran et al. (1993) Acta Neuropathol. (Berl)., 85:362-9) have shown that BChE is present in key brain areas and appears to contribute to the maturation of plaques in AD. BChE co-localization within the amyloid plaques correlates with the conversion of benign plaques to form pathogenic structures associated with neuritic degeneration and dementia. BChE becomes associated with amyloid plaques at approximately the same time that the Aβ deposits assume a compact β-pleated conformation. BChE appears to participate in the change of these plaques from an initially benign form to a malignant form characterized by the neuronal loss and clinical dementia.

Among the earliest and most consistently reported observations in AD brains are profound reduction in the activity of acetylcholinesterase (AChE) and the relationship of AChE levels to the severity of dementia (Schliebs et al. (2006) J. Neur. Trans., 113:1625-44; Francis et al. (1999) J. Neurol. Neurosurg. Psych., 66:137-47; Davies et al. (1976) Lancet, 2:1403; Coyle et al. (1983) Science, 219:1184-1190). The cholinergic hypothesis, which first emerged more than 20 years ago (Davies et al. (1976) Lancet, 2:1403), proposes that dementia, as well as the memory loss and decrease of cognitive functions in AD are caused by diminishing levels of acetylcholine in the brain. While AChE and its inhibition has long been an accepted focal point to therapeutic interventions in AD and a target of radiotracers for mapping acetylcholinesterase in human brain using PET and SPECT (Irie et al. (1996) J. Nucl. Med., 37:649-655; Kilbourn et al. (1996) Synapse, 22:123-131; Kuhl et al. (1996) J. Nucl. Med., 37:21P; Iyo et al. (1997) Lancet, 349:1805-1809; Bencherif et al. (2002) Synapse, 45:1-9; Reed et al. (1999) Neurology, 52:680-682; Herholz et al. (2000) J. Neural Transm., 107: 1457-68; Snyder et al. (2001) J. Cereb. Blood Flow Metab., 21:132-43; Brown-Proctor et al. (1999) Nucl. Med. Biol., 26:99-103), BChE emerged only recently as an important contributor to the occurrence, symptoms, progression and responses to treatment in AD (Lahiri et al. (2004) Curr. Pharm. Des., 10:3111-9; Lahiri et al. (2003) Curr. Drug Targets, 4:97-112; Giacobini et al. (2002) J. Neural. Transm., 109:1053-65; Layer, P. G. (1995) Alzheimer Dis. Assoc. Disord., 9 Suppl 2:29-36; Perry et al. (1978) Neuropathol. Appl. Neurobiol., 4:273-7; Perry et al. (1980) Age Ageing., 9:9-16; Guillozet et al. (1997) Ann. Neurol., 42:909-18; Mesulam et al. (1994) Ann. Neurol., 36:722-7; Namba et al. (1999) Eur. J. Nucl. Med., 26:135-43; Arendt et al. (1992) Neurochem. Int., 21:381-96). Guillozet et al. (Guillozet et al. (1997) Ann. Neurol., 42:909-18) found that although the Aβ plaques are present in brains of demented and normal individuals, the plaques positive for BChE are found only in tissue from AD subjects. Furthermore, BChE activity is found to be associated only with the compact plaques.

More treatment and imaging strategies are concentrated on AChE because this is the enzyme involved in the synaptic function. However, the AChE activity declines in the progressing AD (AChE is lost early by up to 85% in specific AD brain regions (Perry et al. (1978) Neuropathol. Appl. Neurobiol., 4:273-7; Perry et al. (1980) Age Ageing., 9:9-16)) whereas the activity of BChE progressively increases as the severity of dementia advances (Atack et al. (1987) J. Neurochem., 48:1687-92). Thus, it is expected that BChE is better suited as the marker of the AD progression and responses to treatment. The ratio of BChE to AChE increases from within the range of about 0.2-0.5 in normal brain to as high as 11 in regions affected by AD (Giacobini, E. (2001) Drugs Aging, 18:891-8; Giacobini, E. (2003) Int. J. Geriatr. Psychiatry, 18:S1-S5). Advanced plaques show >93% BChE activity, compared with <20% in early diffuse plaques (Perry et al. (1978) Neuropathol. Appl. Neurobiol., 4:273-7; Perry et al. (1980) Age Ageing., 9:9-16; Guillozet et al. (1997) Ann. Neurol., 42:909-18; Mesulam et al. (1994) Ann. Neurol., 36:722-7) suggesting that these prominent longitudinal changes in the BChE activity in plaques are the ideal indicator for the AD staging and for the evaluation of effects of therapeutic interventions.

To date, compounds with the consistent history of effectiveness in treating the cognitive and functional symptoms of AD are cholinesterase inhibitors (Lahiri et al. (2004) Curr. Pharm. Des., 10:3111-9; Giacobini et al. (2002) J. Neural. Transm., 109:1053-65; Weinstock et al. (2006) J. Neural. Transm. Suppl., 70:443-6; Gauthier et al. (2006) Curr. Med. Res. Opin., 22:2251-65; Raschetti et al. (2005) Eur. J. Clin. Pharmacol., 61:361-8; Lopez-Pousa et al. (2005) Dement. Geriatr. Cogn. Disord., 19:189-95; Birks, J. (2006) Cochrane Database Syst Rev., 1:CD005593; Wilkinson et al. (2002) Int. J. Clin. Pract., 56:441-6.). In the majority of clinical trials conducted to date (see Birks, J. (2006) Cochrane Database Syst Rev., 1:CD005593 for review), the outcome is typically evaluated using the Clinician's Interview-Based Impression of Change scale (CIBIC-Plus), the Gottfries, Brane and Steen scale (GBS) or the Global Deterioration Scale (GDS) for the global assessment. Similarly, the cognitive and the daily activity assessments are done using several of the available impairment evaluation methods, all of which are descriptive and carry the risk of some degree of subjectivity. Concerns such as this instigated research into the noninvasive imaging methods that can quantify changes occurring in the AD brain as it deteriorates or responses to the therapeutic intervention (Irie et al. (1996) J. Nucl. Med., 37:649-655; Kilbourn et al. (1996) Synapse, 22:123-131; Kuhl et al. (1996) J. Nucl. Med., 37:21P; Iyo et al. (1997) Lancet, 349:1805-1809; Bencherif et al. (2002) Synapse, 45:1-9; Reed et al. (1999) Neurology, 52:680-682; Herholz et al. (2000) J. Neural Transm., 107: 1457-68; Snyder et al. (2001) J. Cereb. Blood Flow Metab., 21:132-43; Brown-Proctor et al. (1999) Nucl. Med. Biol., 26:99-103; Johnson, K. A. (2006) Curr. Neurol. Neurosci. Rep., 6:496-503). A promising series of benzothiazole derivatives for imaging of amyloid deposits has been recently developed for PET and SPECT imaging (Wang et al. (2004) J. Mol. Neurosci., 24:55-62). Most of the imaging agents designed and tested to date target either amyloid plaques or are substrates for AChE. Because the cerebral amyloidosis precedes AD and does not appear to correlate with clinical or pathological criteria of AD (Wegiel et al. (2007) Acta Neuropathol (Berl)), imaging agents designed to visualize amyloid plaques may not be the best of candidates for imaging of the AD progression. For the same reason these agents are also probably not a good choice as the method to monitor effects of therapy. Radioactive drugs such as for example Pittsburgh Compound-B (Klunk et al. (2004) Ann. Neurol., 55:306-19; U.S. Pat. No. 7,270,800) or FDDNP (Small et al. (2006) N. Engl. J. Med., 355:2652-63) can differentiate between the AD brain and the brain of older individuals with normal cognitive function, even individuals with the mild cognitive impairment, by showing more binding to the brains of patients with AD than in healthy people. However, imaging of the AD progression in a specific patient during the anti-AD therapy using these imaging agents is not expected to be informative.

From the foregoing discussion, it will be appreciated that one of the major challenges in the development of therapeutic strategies to treat AD is the lack of objective, noninvasive methods that can accurately assess the status of the disease before, during and after the treatment.

SUMMARY OF THE INVENTION

The research on which the present invention is based is focused on radioactive drugs able to measure brain levels of BChE. This particular molecule, which is a well established key component of the amyloid plaques, is present in the ever increasing amounts in brains affected by AD, and appears to influence the maturation of plaques in AD ((Lahiri et al. (2004) Curr. Pharm. Des., 10:3111-9; Lahiri et al. (2003) Curr. Drug Targets, 4:97-112; Giacobini et al. (2002) J. Neural. Transm., 109:1053-65; Layer, P. G. (1995) Alzheimer Dis. Assoc. Disord., 9 Suppl 2:29-36; Perry et al. (1978) Neuropathol. Appl. Neurobiol., 4:273-7; Perry et al. (1980) Age Ageing., 9:9-16; Guillozet et al. (1997) Ann. Neurol., 42:909-18; Mesulam et al. (1994) Ann. Neurol., 36:722-7; Moran et al. (1993) Acta Neuropathol. (Berl)., 85:362-9; Schliebs et al. (2006) J. Neur. Trans., 113:1625-44; Francis et al. (1999) J. Neurol. Neurosurg. Psych., 66:137-47; Davies et al. (1976) Lancet, 2:1403; Coyle et al. (1983) Science, 219: 1184-1190; Tasker et al. (2005) Expert Rev. Neurother., 5:101-6). These characteristics position BChE as the imaging target expected to succeed in the evaluation of the AD progression, as well as the excellent surrogate marker of response to therapeutic interventions.

To determine the value of this imaging strategy, the present inventors have designed and synthesized a new class of BChE-selective radiologic agent based on the cycloSaligenyl triesters of 2'-deoxy-3'-fluorothymidine. The affinity of the agents tested to date is directed only towards BChE. There is no detectable cross-reactivity with AChE even at mM levels of these reagents. In light of the role of BChE in central cholinergic transmission and its altered expression in the AD brain, it is believed that radioactive agents with specificity and high reactivity to BChE, a key neuropathological marker of AD, will be valuable in the AD diagnosis, staging and follow-up during the course of therapy.

In accordance with one aspect of the present invention, there is provided a compound of the formula:

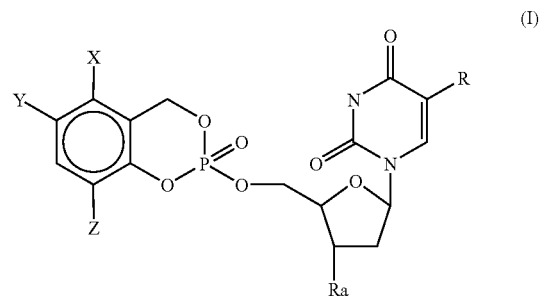

wherein R represents a substituted or unsubstituted, straight or branched chain, saturated or unsaturated, hydrocarbyl ($C_1$-$C_{15}$, particularly $C_1$-$C_8$), radioactive halogen, non-radioactive halogen;

$R_a$ represents radioactive halogen, non-radioactive halogen, hydroxyl;

X represents hydrogen, non-radioactive halogen, radioactive halogen;

Y represents hydrogen, a straight or branched chain, substituted or unsubstituted, saturated or unsaturated, hydrocarbyl ($C_1$-$C_4$), and $^{11}$C-containing analogues thereof; and Z represents hydrogen, straight or branched chain, substituted or unsubstituted saturated or unsaturated, hydrocarbyl ($C_1$-$C_4$), and $^{11}C$-containing analogues thereof.

In another aspect, the present invention provides compositions comprising compounds of formula I and at least one pharmaceutically acceptable carrier medium.

In accordance with still another aspect of the present invention, there is provided a method for making an ante mortem diagnosis of Alzheimer's disease comprising administering to a patient suspected of having Alzheimer's disease a compound of the above formula in an amount effective to bind to butyrylcholinesterase (BChE) present in the brain of said patient; and detecting the amount of BChE bound by said compound.

The present invention also provides a number of synthetic routes for making the compounds of formula (I) above. These syntheses are set forth in the detailed description that follows.

The radioactive compounds of this invention have the unique ability to bind very specifically and irreversibly to BChE, making them highly efficient radiologic imaging agents. These agents are effective for measuring changes in the levels of BChE as AD progresses and as it responds to therapeutic intervention. Obtaining this information noninvasively and at every step in the course of therapy is expected to hasten the development of new improved drugs for the treatment of AD.

BRIEF DESCRIPTION OF THE DRAWINGS

FIG. 4A shows only head areas and FIG. 4B is the whole body image.

FIGS. 10 A,B,C: In addition to individual silver grains seen in control brain (FIG. 9), clusters of silver grains associated with BChE are seen. FIG. 10D: Cross-section of a blood vessel containing red blood cells surrounded by silver grains corresponding to circulating 3.

DETAILED DESCRIPTION OF THE INVENTION

Figure 1:
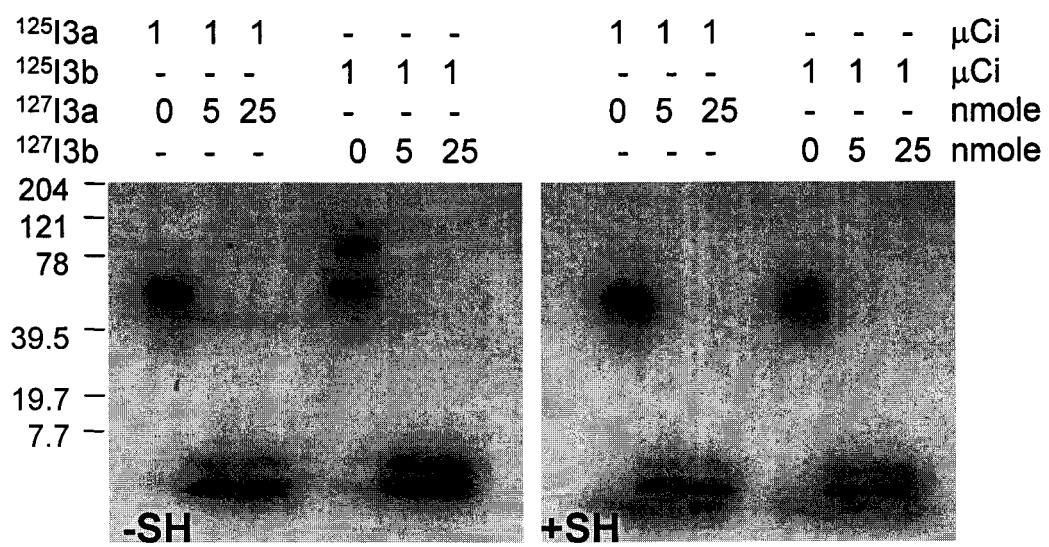
FIG. 1 provides autoradiograms of nondenaturing SDS-PAGE gels run in absence (—SH) or the presence (+SH) of mercaptoethanol.
Figure 2:
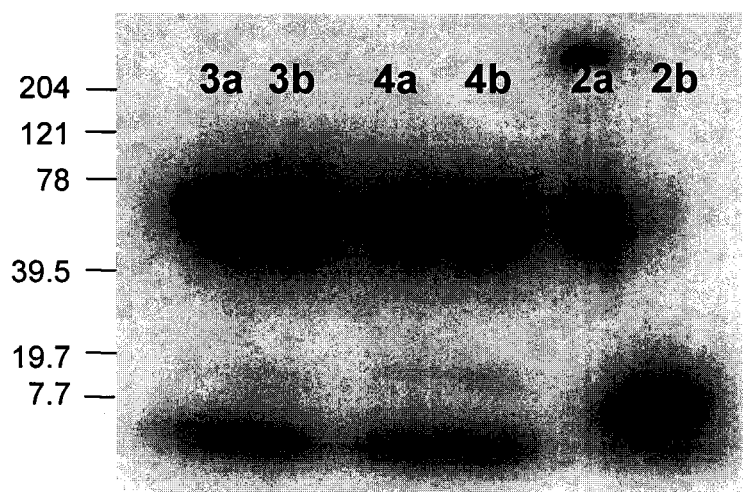
FIG. 2 provides an autoradiogram of the reducing SDS-PAGE of 2, 3, and 4, incubated for 30 minutes with BChE- and AChE-containing mouse serum at 37° C.
Figure 3:
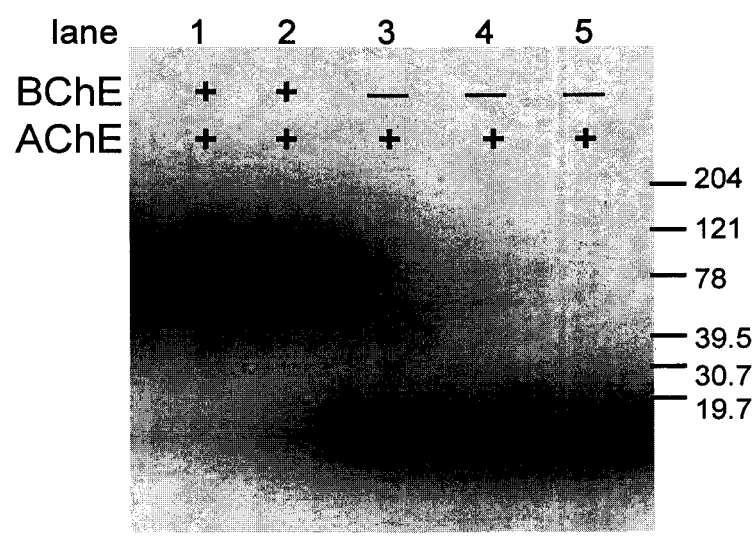
FIG. 3 provides an autoradiogram of SDS-PAGE of 2a incubated with BChE-positive mouse serum and in AChE-positive bovine serum showing specific and strong binding of 2a to BChE. Lanes 1, 2: BChE-containing mouse serum incubated with 2a in (1) PBS+DMSO; (2) PBS+0.1% Triton X100+DMSO. Lanes 3-5: AChE-only containing bovine serum incubated with 2a in (3) DMSO; (4) PBS+DMSO; (5) PBS+0.1% Triton X-100+DMSO.
Figure 4:
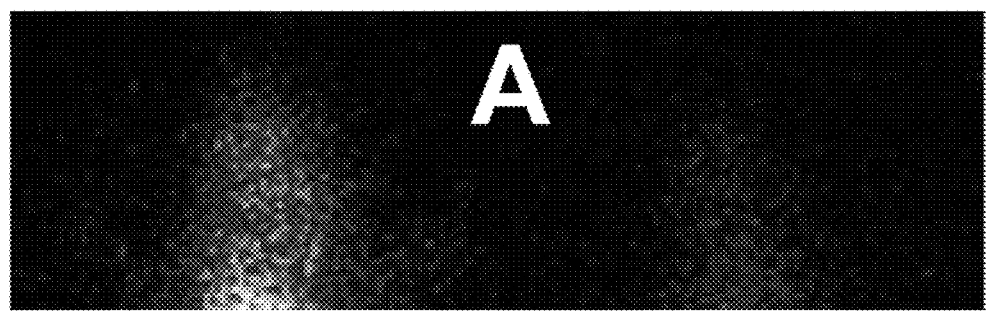
FIG. 4 provides planar images of AD mice acquired 1 hour after IV dose of either 2a or 2b.
Figure 4:
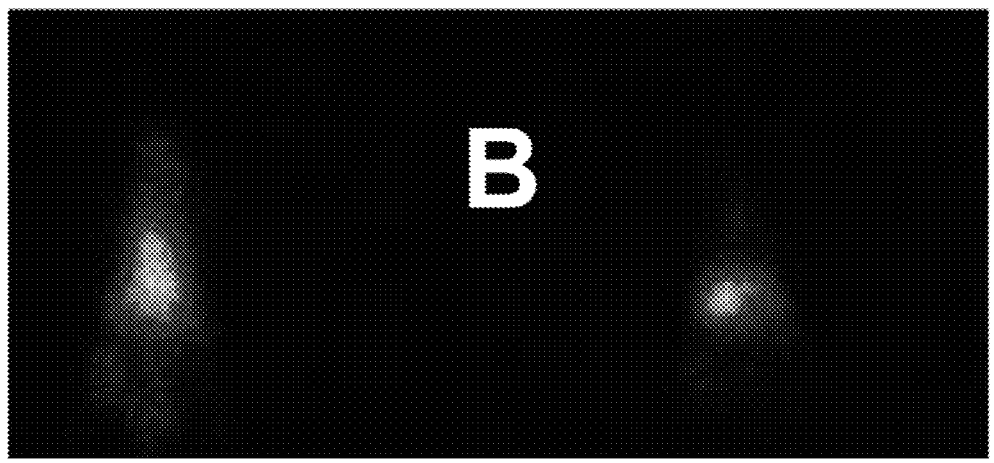
Figure 5:
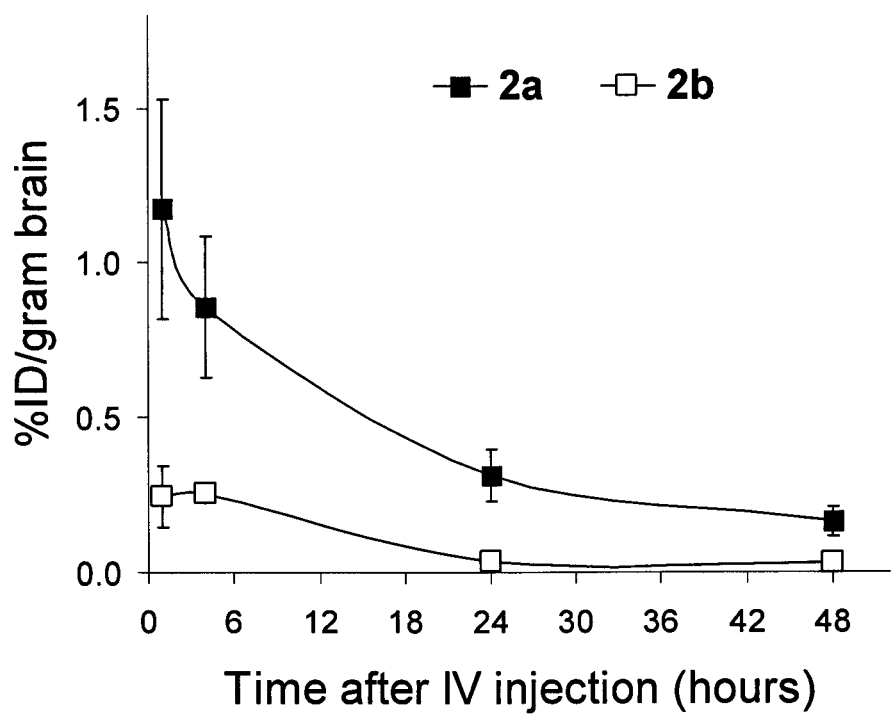
FIG. 5 provides a graph demonstrating the brain clearance curves of 2a (solid squares) and 2b (open squares) in AD mice after IV injection.
Figure 6:
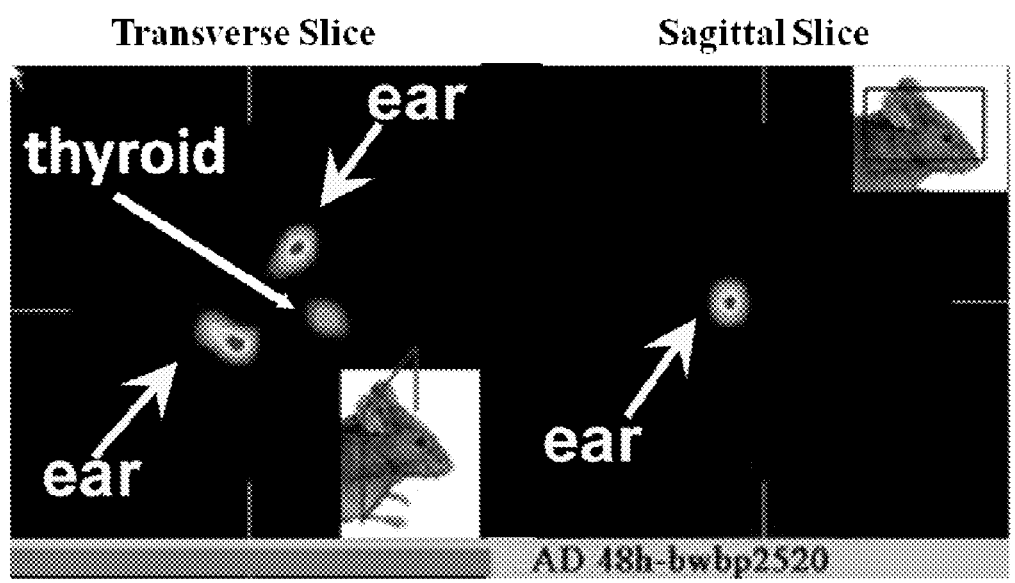
FIG. 6 provides SPECT images of head of 7 months old AD mouse injected IV with 2a 48 hours before the imaging. Left: transverse; right: sagittal view. At 48 hours there is persistent retention of 2a in BChE present in the dorsal ear skin of mice.

In a particular embodiment, the compounds of the instant invention are of formula (I) above, wherein R represents straight or branched chain alkyl ($C_1$-$C_8$) or aryl; $R_a$ represents 18F; X represents F; Y represents branched chain alkyl ($C_1$-$C_4$); Z represents branched chain alkyl ($C_1$-$C_4$). In preferred embodiments, the compound is 5'-O—[cycloSaligenyl-3,5-di(tert-butyl)-6-fluoro]-3'-[$^{18}F$]fluorothymidine monophosphate or 5'-O-[cycloSaligenyl-3,5-di(tert-butyl)-6-fluoro-2', 3'-deoxy-3'-fluoro-5-[$^{125}I$]iodouridine monophosphate.

The compounds of the instant invention comprise radioisotopes, which are preferably gamma-emitting isotopes or positron-emitting isotopes. In a particular embodiment, the radionuclide is a positron emitting isotope of carbon, oxygen, phosphorus, fluorine, chlorine, bromine, or iodine, such as $^{10}C$, $^{11}C$, $^{13}N$, $^{13}O$, $^{14}O$, $^{15}O$, $^{30}P$, $^{17}F$, $^{18}F$, $^{32}Cl$, $^{33}Cl$, $^{34}Cl$, $^{74}Br$, $^{75}Br$, $^{76}Br$, $^{77}Br$, $^{78}Br$, $^{117}I$, $^{118}I$, $^{119}I$, $^{120}I$, $^{121}I$, $^{122}I$, $^{124}I$, $^{126}I$, and $^{128}I$. Gamma radiation-emitting isotopes useful with the method include, but are not limited to, for example, $^{77}Br$, $^{80m}Br$, $^{123}I$, $^{130}I$, $^{131}I$ and $^{125}I$. Preferred radioisotopes for in vivo positron emission tomography (PET) imaging are $^{11}C$ and $^{18}F$. Preferred radioisotope for in vivo single photon emission computed tomography (SPECT) imaging is $^{123}I$.

The diagnostic methods of the invention comprise administering to a patient at least one of the compounds described herein, preferably in a pharmaceutically acceptable carrier. In a particular embodiment, the compound of the instant invention is administered to the patient in an amount of up to 20 mCi (up to 740 MBq). The methods further comprise detecting the binding of the compound to BChE present in the brain of the patient. The diagnostic method may also include the step of comparing the amount of BChE detected to a positive or negative control. In a particular embodiment, the detection of the compound is carried out by gamma imaging, such as positron emission tomography (PET) or single photon emission computed tomography (SPECT).

In a separate embodiment of the instant invention, the method of diagnosing Alzheimer's disease further comprises administering the compound of the instant invention to the patient at least one additional time after a prescribed time interval, the length of which is typically determined by attending medical personnel, and detecting the presence of the compound. Increased binding of the compound is indicative of the progression of Alzheimer's disease in the patient. In yet another embodiment, the compound of the instant invention is administered and detected after the patient has undergone therapeutic treatment for Alzheimer's disease. In this way, the efficacy of the therapeutic treatment can be assessed.

The pharmaceutical compositions of the present invention can be administered by any suitable route, for example, by injection (e.g., intravenously and intramuscularly), by oral, pulmonary, nasal, rectal, or other modes of administration. In preferred embodiments, the compositions of the instant invention are administered intravenously or via the carotid artery.

In still another embodiment of the instant invention, non-radioactive forms of the compounds of the instant invention of formula (I) can be used as a therapeutic agent for the treatment of Alzheimer's disease. At least one compound of the instant invention can be administered to a patient, preferably in a composition comprising at least one pharmaceutically acceptable carrier and, optionally, at least one other therapeutic agent for treating Alzheimer's disease. The non-radioactive compounds of the instant invention can be administered to a patient with Alzheimer's disease in order to inhibit the progression of the disease and/or lessen the severity of the disease. In another embodiment, the nonradioactive form of the compound may be administered to a patient who has not yet been diagnosed with Alzheimer's disease, particularly a patient at risk for Alzheimer's disease, in order to prevent or inhibit the onset of Alzheimer's disease.

DEFINITIONS

The term "hydrocarbyl", as used herein, refers to an unsubstituted or substituted, saturated or unsaturated hydrocarbon radical containing from about 1 to 15 carbon atoms, which may be an aliphatic, cycloaliphatic or aromatic hydrocarbon group. When substituted, hydrocarbyl groups may be substituted at any available point of attachment. When the hydrocarbyl group is said to be substituted with a hydrocarbyl group, this is used interchangeably with "branched hydrocarbyl group". Exemplary unsubstituted hydrocarbon radicals include alkyl groups such as methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, octadecyl, nonadecyl, eicosyl, heneicosyl, docosyl, tricosyl, tetracosyl, pentacosyl, and the like; alkenyl groups such as vinyl, allyl and the like; aromatic groups such as phenyl, tolyl, xylyl, napthyl, biphenyl, and the like; aralkyl groups such as benzyl, phenethyl, phenpropyl, phenbutyl, phenhexyl, napthoctyl, and the like; and cycloalkyl groups such as cyclopropyl, cyclobutyl, cyclohexyl, cycloheptyl, cyclooctyl, and the like. Exemplary substituents may include but are not limited to one or more of the following groups: halo (such as F, Cl, Br, I), alkoxy, alkylthio, hydroxy, carboxy (—COOH), amino (—NH$_2$), monoalkylamine (—NHR), dialkylamine (—NR$_2$), or thiol (—SH), wherein R in the aforementioned substituents represents a hydrocarbyl radical. Hydrocarbyl groups may also be interrupted with at least one oxygen, nitrogen, or sulfur atom.

The terms "halogen," "halo," and "halide" refer to chlorine, bromine, fluorine or iodine.

As used herein, "diagnosis" refers to providing any type of diagnostic information, including, but not limited to, whether a subject is likely to have a condition, information related to the nature or classification of the condition, information related to prognosis and/or information useful in selecting an appropriate treatment. As used herein, "diagnostic information" or information for use in diagnosis is any information that is useful in determining whether a patient has a disease or condition and/or in classifying the disease or condition into a phenotypic category or any category having significance with regards to the prognosis of or likely response to treatment (either treatment in general or any particular treatment) of the disease or condition.

As used herein, the term "positive control" refers to a sample or image of the brain of a patient diagnosed with Alzheimer's disease. Multiple positive controls representing varying degrees of severity of the Alzheimer's disease can be used in the instant diagnostic methods.

As used herein, the phrase "negative control" refers to a sample or image of the brain of a normal or healthy patient who has not been diagnosed with Alzheimer's disease.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween 80, Polysorbate 80), emulsifier, buffer (e.g., Tris HCl, acetate, phosphate), antimicrobial, bulking substance (e.g., lactose, mannitol), excipient, auxilliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, 20th Edition, (Lippincott, Williams and Wilkins), 2000; Liberman, et al., Eds., Pharmaceutical Dosage Forms, Marcel Decker, New York, N.Y., 1980; and Kibbe, et al., Eds., Handbook of Pharmaceutical Excipients (3$^{rd}$ Ed.), American Pharmaceutical Association, Washington, 1999.

The term "leaving group" refers to an atom or substituent capable of being displaced by a nucleophile. Exemplary leaving groups include, without limitation, halogen (e.g., chloro, fluoro, bromo, iodo), alkylsulfonyl, substituted alkylsulfonyl, arylsulfonyl, substituted arylsulfonyl, heterocyclcosulfonyl, and trichloroacetimidate, p-(2,4-dinitroanilino)benzenesulfonyl, benzenesulfonyl, methylsulfonyl (mesylate), p-methylbenzenesulfonyl (tosylate), nosyl, p-bromobenzenesulfonyl, trifluoromethylsulfonyl (triflate), trichloroacetimidate, acyloxy, 2,2,2-trifluoroethanesulfonyl, imidazolesulfonyl, and 2,4,6-trichlorophenyl groups.

The term "protecting group" refers to an atom or a substituent that reduces or prevents the reactivity of a reactive group in a molecule. Examples of protecting groups can be found in T. W. Greene and P. G. Futs, Protective Groups in Organic Chemistry, (Wiley, 2nd ed. 1999); Beaucage, et al. (1992) Tetrahedron, 12:2223; and Harrison and Harrison et al., Compendium of Synthetic Organic Methods, Vols. 1-8 (John Wiley and Sons. 1971-1996). Exemplary protecting groups include, without limitation, t-butyldimethylsilyl (TBDMS), t-butyldiphenylsilyl (TBDPS), dimethoxytrityl (DMT), monomethoxytrityl (MMT), 2,4-dimethoxybenzyl, and t-butyloxycarbonyl.

The following examples provide illustrative methods of practicing the instant invention, and are not intended to limit the scope of the invention in any way.

Example 1

The radiosyntheses of cycloSaligenyl-phosphotriesters of 5-[$^{125}$I]iodo-2'-deoxyuridine 2-4 (cycloSal-triesters) is described herein. The separation of compounds 2-4 into their respective S$_P$ and R$_P$ diastereoisomers 2a, 3a, 4a and 2b, 3b, 4b is also described herein. Biodistribution and SPECT imaging studies using these cycloSal-triesters in normal and transgenic mice were conducted to assist in the selection of the best candidate compounds for further studies. Structures are shown in Scheme 1 and 2.

Scheme 1

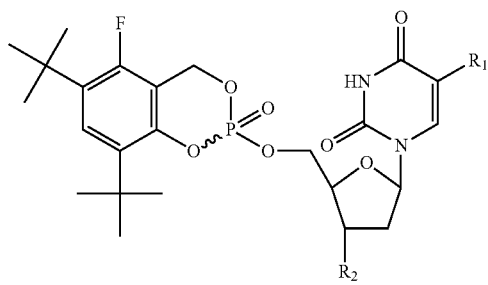

$R_1 = CH_3, R_2 = {}^{18}F$  $R_1 = {}^{125}I, R_2 = F$
1  $S_P/R_P$ mixture   11  $S_P/R_P$ mixture
1a  $S_P$ diastereomer  11a  $S_P$ diastereomer
1b  $R_P$ diastereomer  11b  $R_P$ diastereomer

Scheme 2

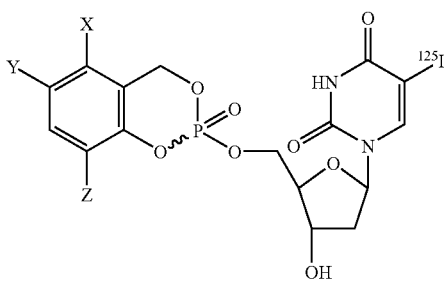

X = F, Y = Z = t-butyl
  2  ($S_P/R_P$ mixture)
  2a ($S_P$ diastereomer)
  2b ($R_P$ diastereomer)
X, Y, Z = H
  3  ($S_P/R_P$ mixture)
  3a ($S_P$ diastereomer)
  3b ($R_P$ diastereomer)
X, Y = H, Z = $CH_3$
  4  ($S_P/R_P$ mixture)
  4a ($S_P$ diastereomer)
  4b ($R_P$ diastereomer)

Syntheses of $^{125}$I-Labeled BChE-Binding Compounds.

First, nonradioactive [$^{127}$I]iodo-analogs were synthesized in a phosphorus(III) route as follows: cyclic chlorophosphites, prepared from the appropriate salicyl alcohols (Meier et al. (1998) Eur. J. Org. Chem., 837-846; Meier et al. (1999) J. Med. Chem., 42:1615-1624), were reacted with 5-iodo-3'-O-levulinyl-2'-deoxyuridine in the presence of diisopropylethyl amine (DIPEA) followed by a direct, one-pot oxidation with t-BuOOH to give phosphates. The subsequent stannylation in the presence of Pd(II) catalyst afforded 5-trimethyl-stannyl-2'-deoxyuridines. Radioiododestannylation (Crisp, G. T. (1989) Synthetic Comm., 19:2117-23; Wigerinck et al. (1993) J. Med. Chem., 36:538-43) led to the no-carrier-added cycloSal-triesters 2-4. A standard stannylation/radio-iododestanylation method (Baranowska-Kortylewicz et al. (1994) J. Labelled Compds. Radiopharm., 34:513-521; U.S. Pat. No. 5,468,853) originally developed for the synthesis of $^{125}$IUdR was successfully used to prepare $^{125}$I-cycloSal-triesters. The high hydrophobicity of new compounds allowed the use of milder reaction conditions, i.e., a very efficient trimethylstannylation was obtained in ethyl acetate at 60° C. instead of the typically employed dioxane at ~110° C. This reduced the extent of dehalogenation from 25% observed at high temperatures to <5% at 60° C. Optimized amounts of the catalyst dichlorobis-(triphenylphosphine)palladium(II), consistently furnished 2-4 in high yield (74-80%). All nonradioactive analogs were fully characterized and their structures confirmed by $^1$H, $^{13}$C, $^{31}$PNMR and FAB. The water solubility of cycloSal-triesters is low and consequently the radioiododestannylation was performed in acetonitrile. Routinely the radiochemical yield of >90% was obtained.

Purification of Radiolabeled Reagents.

The formation of phosphates proceeds without stereoselectivity, therefore radioactive cycloSal-triesters 2-4 were first isolated as pairs of diastereomers, ~1:1 mixtures with respect to the configuration at the phosphorus center. It was anticipated that each of these two diastereomers having different hydrophobicity and rates of hydrolysis may also exhibit different biological activities. Therefore, diastereomers were separated during the HPLC purification and all radioactive products were available for testing as pure $S_P$ and $R_P$ isomers. The $S_P$ and $R_P$ assignment of configuration for 2-4 is based on the correlation of the elution properties from the $C_{18}$ column, $^{31}$PNMR chemical shift, and the assignment of configuration employed by Meier (Meier, C. (2002) Mini Rev. Med. Chem., 2:219-34) for cycloSal-2',3'-didehydrothymidine and the CD-spectroscopy of cycloSal-(-)-menthyl-monophosphates as the reference compounds.

Syntheses of Key Reagents and Intermediates for PET Imaging Reagents.

The focus of this portion of the studies was on the preparation of intermediates needed for the efficient and rapid synthesis of the target compound, 5'-O-[cycloSaligenyl-3,5-di(tert-butyl)-6-fluoro]-3'-deoxy-3-[$^{18}$F]fluorothymidine monophosphates 1 and also on the preparation of the nonradioactive analytical standards to be used later in the verification of the identities of radiofluorinated products. Pathway 1, described in detail herein below, requires a direct coupling of the appropriate cyclic chlorophosphite with $^{18}$FLT to give 1.

5'-O-[cyclo-Saligenyl-3,5-di(tert-butyl)-6-fluoro)]-2', 3'-deoxy-3'-fluoro-5[$^{125}$I]iododeoxyuridine Monophos-Phates 11

First, 5 and 9 were stannylated to give the corresponding 2',3'-dideoxy-3'-fluoro-5-trimethyl-stannyluridines 6 and 10. These were radioiododestannylated to give compounds 7 and 11 in ~95% yield. Diastereoisomers $S_P$ (11a) and $R_P$ (11b) were resolved to 100% purity on HPLC. Radiolabeled 11 was also prepared via radioiododestannylation of 10 (Scheme 3, path b) to serve as the independently synthesized analytical standard.

Radiochemical yields of 11 obtained via a direct coupling of 7 with chlorophosphite (Scheme 3, paths c,d,e) allows for the prediction that similarly good yields can be obtained in the synthesis of $^{18}$F-labeled 1, which can be prepared under the same set of conditions. The top overall radiochemical yield of 11 when prepared from 7 (~40%) was routinely obtained when crude saligenyl chlorophosphite was first treated with diisopropylamine (DIPA) to generate corresponding saligenyl N,N-diisopropylaminophosphoramidite and when the subsequent coupling with 7 was activated with $^1$H-tetrazole.

The described above sequence is fully applicable to the preparation of $^{18}$FLT cycloSal-triesters 1 shown in Scheme 1. Physical and chemical properties of 11 mimic these of fluorinated thymidine. Moreover, the concentrations employed in this direct coupling method are comparable to concentrations that are attainable in radiofluorinations.

Scheme 3

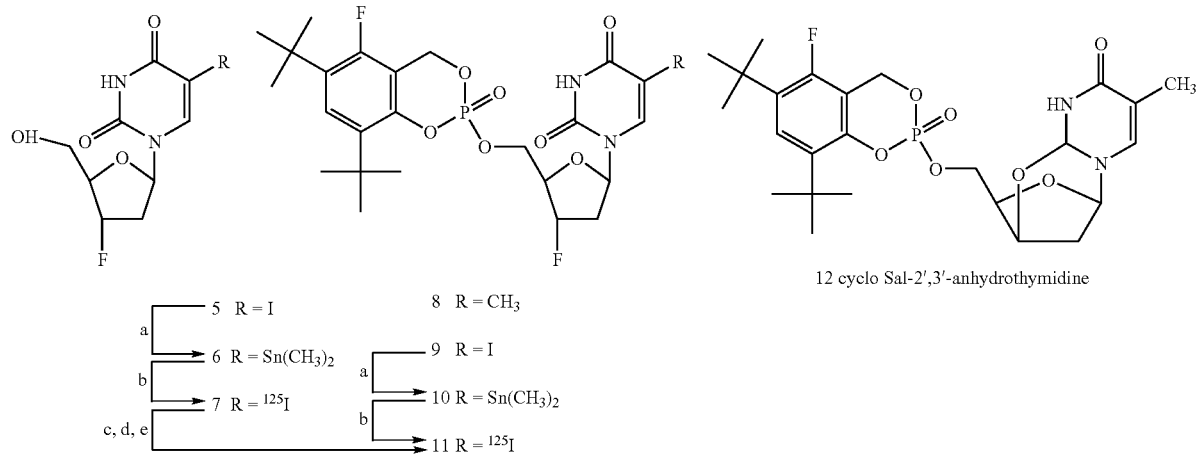

12 cyclo Sal-2′,3′-anhydrothymidine

- 5  R = I
- 6  R = Sn(CH₃)₂
- 7  R = ¹²⁵I
- 8  R = CH₃
- 9  R = I
- 10 R = Sn(CH₃)₂
- 11 R = ¹²⁵I

Reagents and conditions: (a) Sn₂(CH₃)₂, (1.6 equiv) in ethyl acetate, 60° C., (Ph₃P)Pd(II)Cl₂(0.06 equiv), 2 h; (b)Na¹²⁵I/NaOH, 30% H₂O₂, TFA/CH₃CN(0.1% v/v), 20 min, HPLC purification; (c) cycloSal-3,5-di(tert-butyl)-6-fluoro)-chlorophosphite in CH₃CN; (d) DIPA; (e) 1-H-tetrazole (0.45 M solution in CH₃CN), -40° C. ⟶ rt.

5′-O-[cycloSaligenyl-3,5-di(tert-butyl)-6-fluoro]-3′-deoxy-3′-fluorothymidine 8

This non-radioactive standard of target compound 1 was prepared using thymidine and conditions suitable for radiofluorination as follows: after protection of the 5′-hydroxyl with the dimethoxytrityl group, the configuration at the 3′-position was inverted by mesylation and the subsequent hydrolysis of a crude mesylate analog. Next, the treatment with N,N′-diethylaminosulfur trifluoride (DAST) in a mixture of $CH_2Cl_2$-THF and detritylation with HCl in $CH_3CN$ afforded 3′-deoxy-3′-fluorothymidine in 52% overall yield. The reaction with chlorophosphite, using conditions described above for the preparation of 2-4, produced 8 in 61% yield, as a diastereomeric mixture. Individual isomers were successfully separated on HPLC. The same HPLC conditions can be used to separate $S_P$ and $R_P$ stereoisomers of $^{18}F$-labeled 1.

Synthesis of 5′-O-[cycloSaligenyl-3,5-di(tert-butyl)-6-fluoro]-2′,3′-anhydrothymidine 12

Derivatives of 2′,3′-anhydrothymidines are susceptible to nucleophilic attack by various nucleophiles leading to a range of 3′-deoxy-3′-substituted thymidines with the substituent at the 3′-exo-sugar ring position (Machulla et al. (2000) J. Radioanal. Nucl. Chem., 243:843-846). Low nucleophilicity and non-carrier added concentrations of [18F]fluoride require high temperatures for the anhydro-ring to open and for the substitution to occur. However, the simplicity of the protection strategy of 11 whereby the anhydro unit acts simultaneously as the leaving group and as the protecting group prompted the preparation of this precursor to be tested in Pathway 2. To accomplish this, thymidine, protected with the 4,4′-dimethoxytrityl group (DMTr) at the 5′-position, was reacted with levulinic acid and DCC in the presence of 4-dimethylaminopyridine (DMAP) in $CH_2Cl_2$. Subsequent deprotection of the DMTr group (Sharma et al. (2003) J. Org. Chem., 68:4574-4575) yielded 3′-levulinate in nearly quantitative yield. The coupling of 3′-levulinate with cyclic chlorophosphite in a presence of DIPEA and the oxidation of the formed phosphite triester using t-BuOOH, gave 3′-protected triphosphate, which after a silica gel purification and the cleavage of the levulinic group with hydrazine hydrate in a pyridine/acetic acid mixture at room temperature gave cycloSal-triester of thymidine in 56% overall yield. The next two steps: mesylation with methanesulfonyl chloride/triethylamine and the cyclization, with 1,8-diazabicyclo-[5.4.0]undecane (DBU) were performed subsequently without separation of the mesylated intermediate, to give 12 in 69% yield.

Binding of New Drugs to BChE.

Mice serum, which has high levels of BChE (Doctor et al. (1990) FEBS Lett., 266:123-7; Arpagaus et al. (1991) J. Biol. Chem., 266:6966-74) and very low levels of AChE was used for this study. All new drugs were tested in a similar manner. Data for 3a and 3b is shown. Aliquots of serum were placed in tubes and nonradioactive $^{127}$I-3a and $^{127}$I-3b was added (0, 5 and 25 nmole). Selected duplicate tubes received either 1 µCi 3a or 1 µCi 3b. One µCi of no-carrier-added drug is equal to 0.45 pmole. Samples were process either by TCA precipitation or gel electrophoresis (FIG. 1). For TCA precipitation tubes were placed in an ice bath and incubated on for 20 minutes. Ice-cold 20% TCA was added to each tube. Protein pellets were separated by centrifugation. Radioactivity associated with the protein pellet, i.e., BChE-bound 3a and 3b, was measured in a γ counter. The recovery of >90% radioactivity in the protein pellet containing BChE indicated that binding of 3a and 3b to BChE is strong. Similarly treated mouse serum samples were also analyzed using SDS-PAGE. Samples were either subjected to mercaptoethanol (+SH) or were left unreduced (−SH). The —SH panel of FIG. 1 shows the autoradiogram of nonreducing gel; the +SH panel shows the corresponding samples run under reducing conditions. The addition of nonradioactive derivatives to serum and brief incubation before the addition of the radioactive compounds effectively blocked the binding. These data clearly point to the stoichiometric, strong and long-lasting binding of new drugs to BChE. It is noteworthy that 3b recognizes binding sites in two forms of BChE whereas 3a binds only to the monomer. Mercaptoethanol reduces the dimer to monomer to which both isomers bind the same way (FIG. 1, +SH). The binding site sensitivity to the configuration of the ligand is even more pronounced in the case of 2a and 2b derivatives, where the $S_P$ diastereomer 2a recognizes BChE binding site and the $R_P$ diastereomer 2b does not bind to BChE at all. FIG. 2 shows the interactions of BChE from mouse serum with certain prepared derivatives and analyzed on the same gel after 30 minutes incubation with mouse serum.

Diastereomers that bind to BChE in mouse serum do not bind to bovine serum, which has very high levels of AChE but no detectable BChE (data for compounds 2a and 2b is shown in FIG. 3). Cholinesterase purified from fetal bovine serum has in its N-terminal sequence of the catalytic subunit no amino acids matching the same sequence of human or mouse BChE (Doctor et al. (1990) FEBS Lett., 266:123-7). Lockridge et al. (Arpagaus et al. (1991) J. Biol. Chem., 266:6966-74) analyzed BChE levels in plasma and serum from various vertebrates and found no BChE activity in serum of cow and sheep. Data presented in FIG. 3 supports their conclusion and underscores the exquisite selectivity of 2a for BChE as evidenced by the complete absence of 2a binding to bovine serum (lanes 3, 4, 5 in FIG. 3), which has very high levels of AChE, is often used as an excellent source of AChE but lacks BChE. FIG. 3 also illustrates that the addition of 0.1%-0.5% DMSO does not interfere with binding of 2a to BChE. The solubility of 2a in buffers and other physiologically appropriate solvents is low and requires the addition of co-solvents.

Thus, 3a, the $S_P$ stereoisomer, binds BChE dimers and monomers present in mouse serum (FIG. 1) whereas the $R_P$ stereoisomer 3b binds only the monomer. It was also found that 2a, the $S_P$ stereoisomer, binds to monomer and to what may be a tetramer (or some other large form) of BChE, whereas 2b does not bind to BChE at all providing an excellent control reagent (FIG. 3).

Partition Coefficients.

In order to reach intracerebral targets, drugs developed for diagnosis of the AD must be able to cross two barriers separating the central nervous system (CNS) from the periphery (Hansch et al. (1987) J. Pharm. Sci., 76:663-87.), the blood-brain barrier and the blood-cerebrospinal fluid barrier. Therefore the preliminary evaluation of the new drugs included partition coefficients. CNS agents that are highly lipid soluble with the log octanol-water partition coefficient between 1 and 3 have the equilibration half-times that are proportional to brain solubility (Atkinson et al. (2002) Curr. Med. Chem., 2:229-40; Dutta et al. (1998) Br. J. Anaesth., 81:422-4; Buchwald et al. (1998) Curr. Med. Chem., 5:353-80). Only pure $S_P$ and $R_P$ diastereomers were used. Ten μCi of each $^{125}$I-labeled compound was added to 3 mL of water, the mixture was vortexed and 1-mL aliquots were transferred into fresh tubes. To each tube 1 mL of 1-octanol was added and the mixtures were vigorously vortexed until a homogenous suspension formed. At this point, the organic and water layers were separated by centrifugation at 19° C. Aliquots of each phase were gently removed and counted in a gamma counter in a triplicate. Typically, each $K_P$ was calculated as an average of n≥18. Average $K_P$ values are listed in Table 1.

TABLE 1

Partition coefficient determined by the shake-tube method using 1-octanol and water layers.

| | P avg (std dev) | log P |
|---|---|---|
| 3a | 4.19 (0.12) | 0.623 |
| 3b | 4.49 (0.25) | 0.652 |
| 4a | 7.19 (0.37) | 0.857 |
| 4b | 7.02 (0.34) | 0.846 |

In the case of 3a and 3b there is a clear difference in their hydrophobicity (P=0.0001). Within the experimental error of this method, no differences between 4a and 4b (P=0.09) was detected. Both derivatives have log P values below the value of 2 taken as the optimal log P for the brain-targeting agents. Nevertheless biodistribution studies indicate that these drugs penetrate BBB and warrant development of structurally similar more lipophilic analogs. Accordingly, it appears that based on the $K_P$ criteria 2a and 2b are good candidates although analysis of partition coefficients for 2a and 2b was not possible using the octanol-water method because both diastereomers are excessively hydrophobic. The estimated log P for agents 2a and 2b is >2.

Biodistribution Studies.

Two sets of preliminary biodistribution studies were conducted: (1) in normal athymic mice to determine general biodistribution and the brain uptake; and (2) in at least ~7-14 months old APPswe mice (strain B6C3-Tg(APPswe, PSEN1dE9)85 Dbo/J; abbreviated as AD mice in the text below). JAX® GEMM® Strain wildtype mice from the colony were used as the control. B6C3-Tg(APPswe, PSEN1dE9) 85 Dbo/J is a double transgenic mice expressing chimeric mouse/human amyloid precursor protein(Mo/Hu APP695swe) and a mutant human presenilin 1(PS1-dE9) both directed to CNS neurons. Both mutations are associated with the early onset AD. Aβ plaques are produced in these mice in hippocampus and cortex by 9 months of age with the occasional deposits found in mice as young as 6 months of age (Jankowsky et al. (2004) Hum. Mol. Genet., 13:159-70; Garcia-Alloza et al. (2006) Neurobiol. Dis., 24:516-524). Planar imaging was done using a pinhole gamma camera. FIG. 4 shows the image of AD mouse acquired 1 hour after the tail vein IV administration of 0.5 mCi 2a or 2b. In both images mice are positioned with the dorsal surface of the mouse facing the pinhole collimator. There is a significant difference in the whole body distribution and retention of 2a compared to 2b. The most noteworthy difference is the accumulation of 2a in the head of the AD mouse (FIG. 4A, left). The head of AD mouse treated with 2b shows only the background level of activity. Diastereomer 2b binds BChE whereas 2b does not (FIG. 2). Brain clearance curves for 2a or 2b are shown in FIG. 5. There were 6 mice per each time point. Percent injected dose per gram brain is significantly higher for 2a at all time points, which is indicative of the significantly increased levels of BChE in brain of these mice.

SPECT images were acquired using a dedicated Animal SPECT Imaging System (Gamma Medica Instruments, Northridge, Calif.) and reconstructed using LumaGEM ver.5.107 with the Butterworth bandpass post-reconstruction filtering. FIG. 6 shows transverse and sagittal views of the head and neck area of 7-months old AD mouse 24 hours after IV administration of 2a (23.4 MBq). SPECT resolution allowed for the clear identification of the uptake of 2a in ears. The transverse view in FIG. 6 shows the retention of 2a in both ears. The significance of the 2a uptake in ears comes from studies by Fitzgerald et al. (McLoughlin et al. (1989) J. Anat., 167:215-23; Cunningham et al. (1972) J. Anat., 112: 93-7), who identified the abundance of BChE activity in mouse's dorsal ear skin. The data provided here clearly shows that 2a binds only to BChE and, therefore, it can be conclude that the uptake seen in ears of these mice is exclusively because of the interactions of 2a with BChE. It should also be noted that BChE in the ear dorsal skin is strictly a characteristic of rodents. Biodistribution studies were also conducted on 3, another BChE-binding derivative, in AD mouse and in normal controls. This study of 3 was conducted in >12-months old AD mice and matching control mice. All mice received IV 10 μCi of 3. Mice were killed 48 hours later. Tissues were collected and their radioactive content determined in a γ counter. One-half of each brain was fixed. The radioactivity in the other half was counted in a γ counter.

Figure 7:
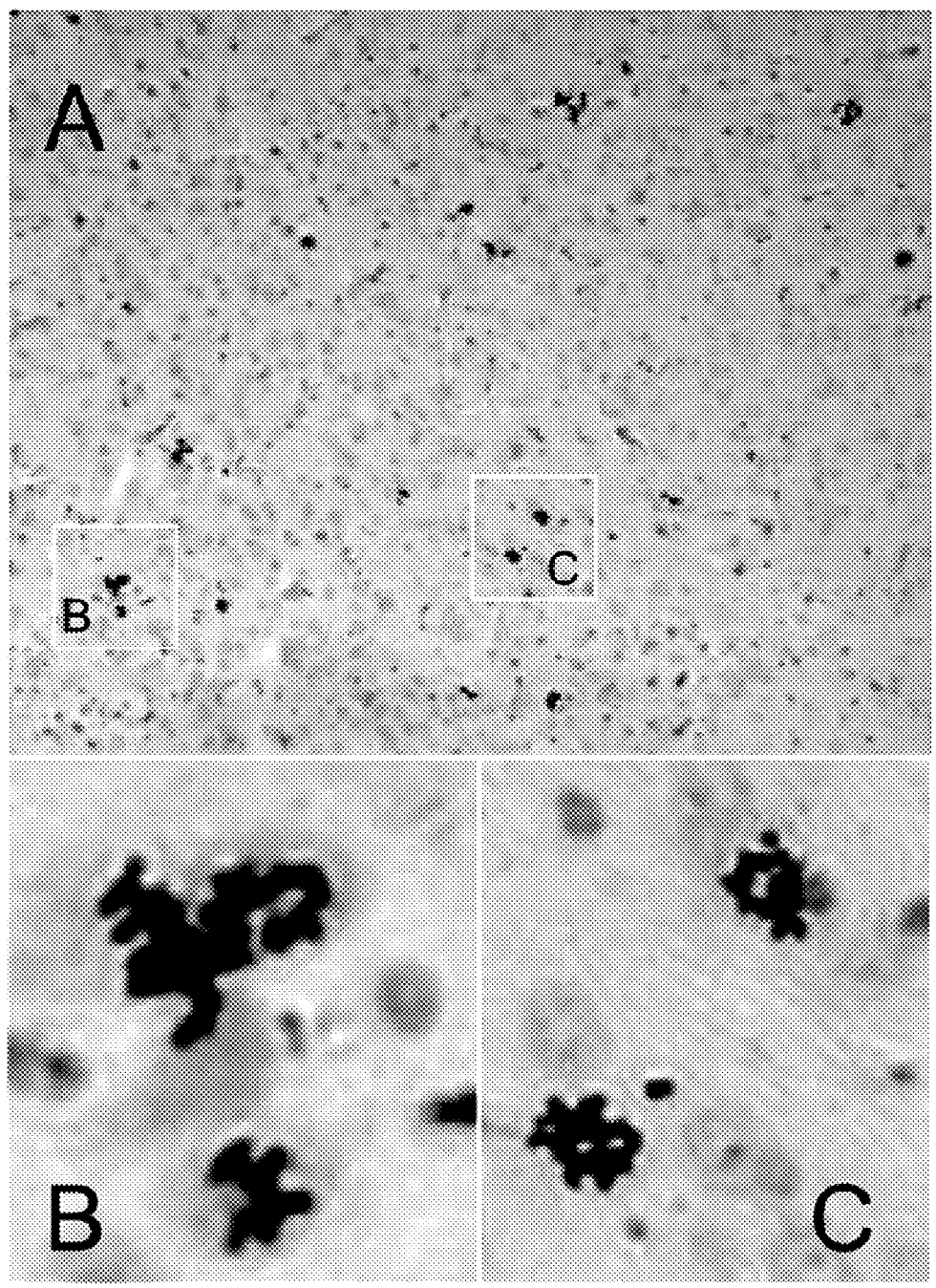
FIG. 7 provides images of microautoradiography of brain sections of AD mouse treated with IV dose of 0.5 mCi 3. Mouse was killed 48 hours after the administration of 3. Counterstained H&E; 10×.
Figure 8:
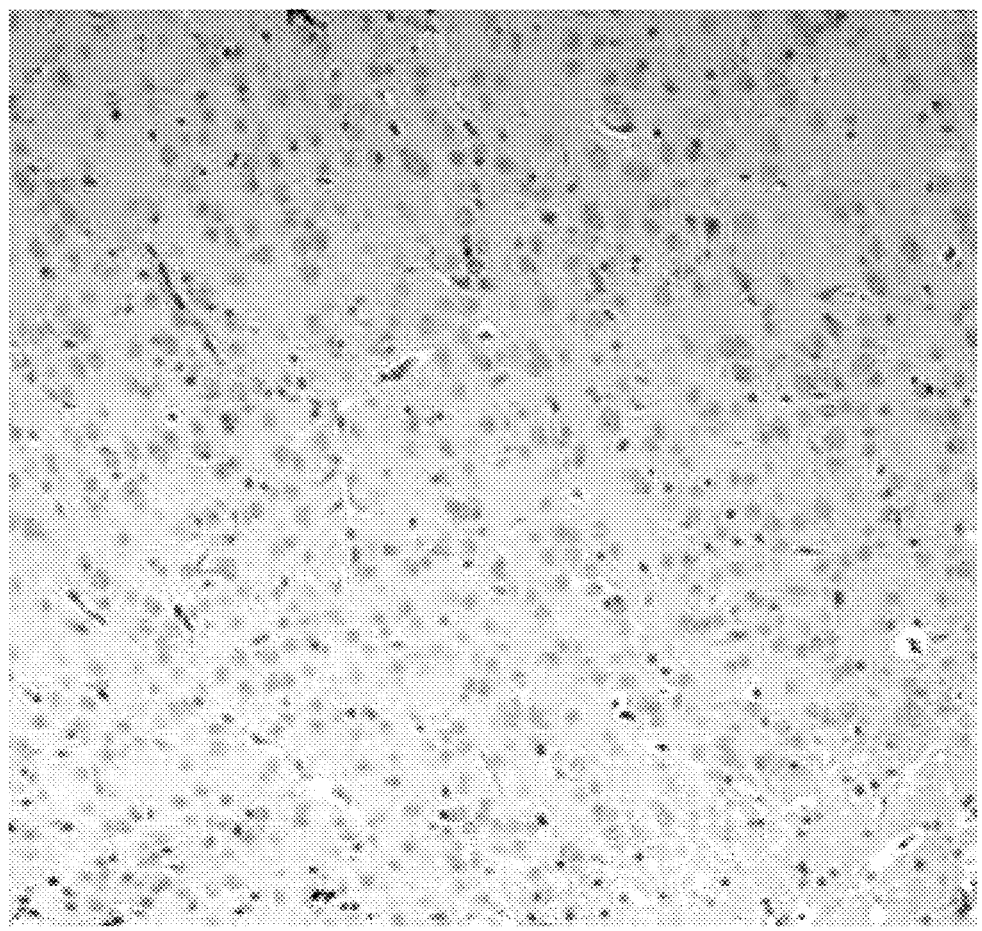
FIG. 8 provides a microautoradiography of brain sections of the matching control mouse also treated with IV doses of 0.5 mCi 3. Mouse was killed 48 hours after the administration of 3. Counterstained H&E; 10×.
Figure 9:
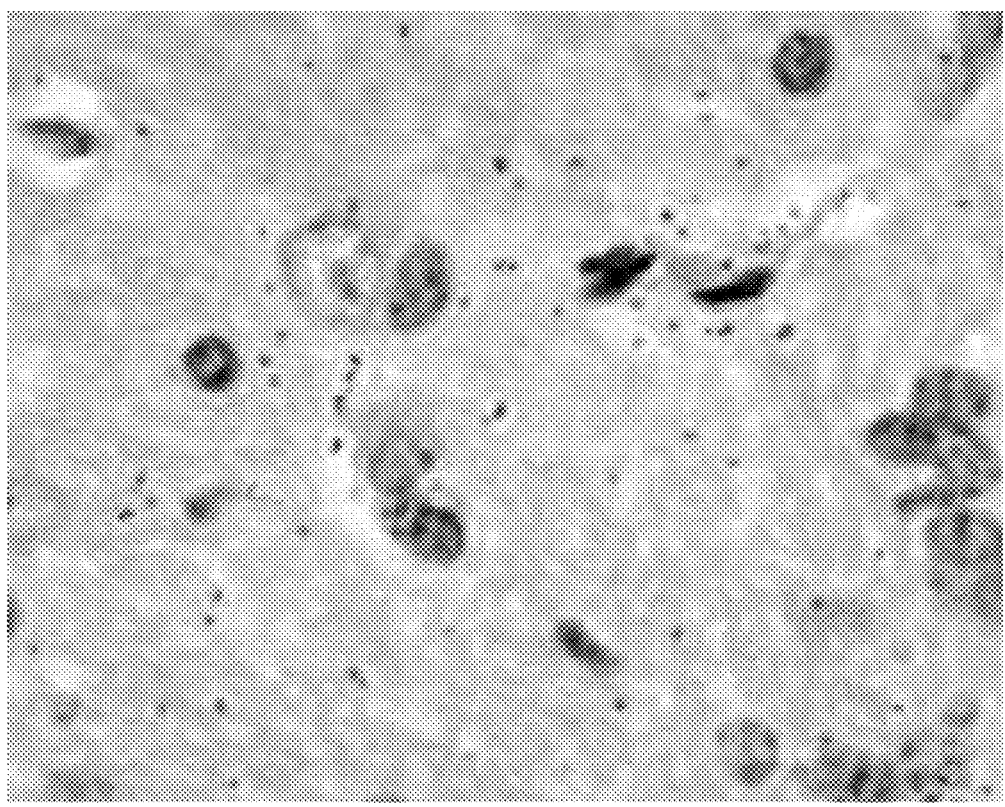
FIG. 9 provides an image of a section of brain from control mouse treated with 3 48 hours before necropsy. 100×; H&E.
Figure 10:
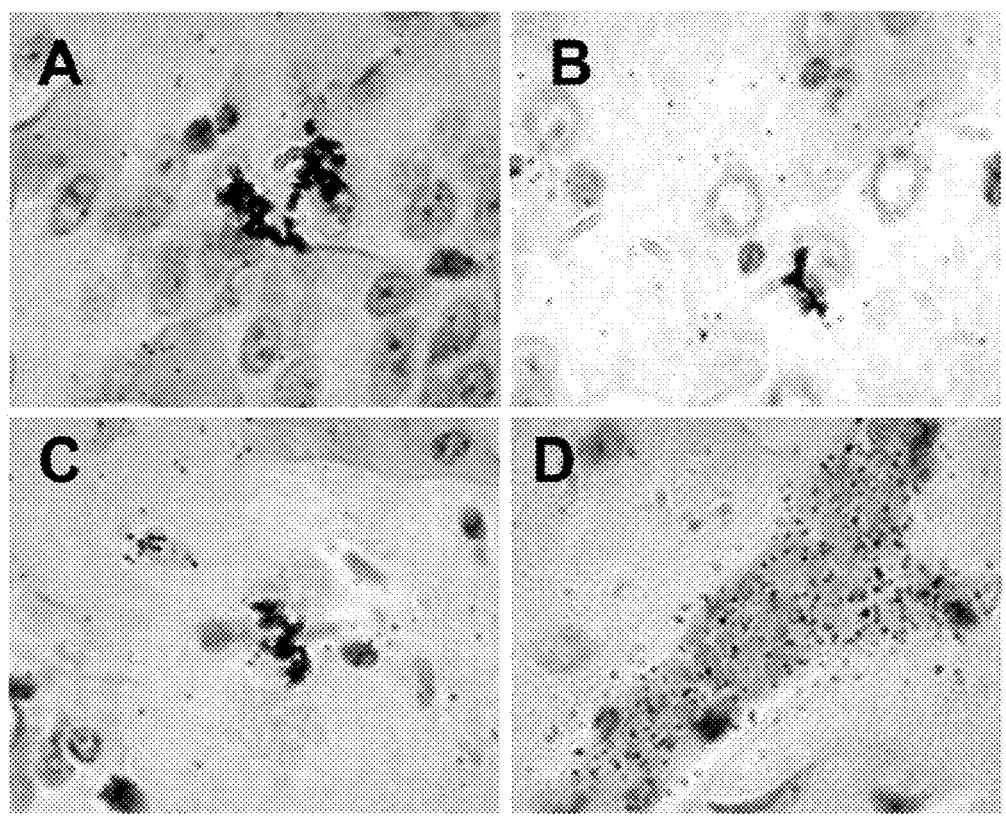
FIG. 10 provides images of brain sections from AD mouse 48 hours after IV dose of 0.5 mCi 3. 100×; H&E.

Significantly, 48 hours after IV administration of 3 the brain uptake was ~3 times higher in AD mice compared to the matching wildtype controls, i.e., in AD mice brain uptake was 0.085±0.008% ID/g compared to 0.030±0.011 in controls (P<0.001). Microautoradiography revealed large clusters of radioactivity in the brain of AD mice. These clusters were practically absent in brains of the control mice. FIG. 7 shows the brain section of AD mouse treated with 3. FIG. 8 is the corresponding section of a brain from a matched control mouse treated in the same manner. AD brain shows numerous large clusters of silver grains (black deposits in this photograph). Similar structures are missing from the brain of a control mouse. The examination of the same sections at a higher magnification reveals multiple individual black silver grains in both brains (FIGS. 9 and 10), however, only AD brain has in addition to the individual silver grains also large intense masses of the deposited silver (FIGS. 10A,B,C). These groupings of deposited silver grains correspond to 3 bound to BChE associated with amyloid plaques. In FIGS. 8 and 10D, multiple grains can be seen associated with the blood vessel in brains of the control and AD mouse, respectively, which correspond to 3 in blood. Imperfections in focus are because brain sections and silver grains are in different planes, tissue section vs. emulsion.

Microautoradiography studies in combination with the imaging and biodistribution studies indicate that the new derivatives selectively recognize and target BChE in brains of AD mice. $^{18}$F-labeled reagents for PET should provide more sensitivity than radioiodinated drugs. In general PET systems also provide better spatial resolution. They also allow for the quantification of tracer concentration in absolute units and recording the changes in expression of specific receptors or metabolic sites, which may prove invaluable in the evaluation of the AD response to treatments or in longitudinal studies of the AD progression.

The drugs proposed herein recognize and bind to BChE, one of the AD companion molecule clearly associated with the risk of developing dementia of the Alzheimer's type. The changes in BChE activity in response to anti-AD therapies are already firmly established. Brains of people with AD show a positive relation between the BChE levels and the Aβ plaque load. In several animal studies, selective inhibition of brain BChE have been shown to improve cognition, to lead to increases in cerebral acetylcholine levels compared with controls, and to stimulate the memory-forming systems. Grieg et al. (Greig et al. (2005) Proc. Natl. Acad. Sci., 102:17213-8) also noted significantly lower Alzheimer beta-amyloid peptide load after treatment with the BChE inhibitor. In summary the PET imaging drugs, which can track changes in the BChE activity in the brain of AD patients, will open a unique and innovative path to measuring AD-related neurodegeneration as well as the response to therapeutic interventions. It is also likely that based on these studies new and even more effective BChE-directed therapies can be developed.

Example 2

$^{18}$FLT is being developed (Grierson et al. (1998) J. Nucl. Med., 39: 22; Grierson et al. (1999) J. Labelled Comp. Radiopharm., 42:5525-5526; Grierson et al. (1999) J. Nucl. Med., 40:83P; Griersn et al. (1997) J. Labelled Compd. Radiopharm., 40:60-62; Grierson et al. (1998) J. Nucl. Med., 39:229P; Rasey et al. (1999) J. Nucl. Med., (40)5:25P; Shields et al. (1998) Nat. Med., 4:1334-1336) as a PET imaging agent of proliferating cells in cancer. The results presented herein highlight a new application for derivatives of 18FLT in the form of cycloSal-3'-deoxy-3'-[$^{18}$F]fluorothymidine monophosphates 1 as novel PET tracers specific to the BChE content in the brain of AD patients. 5'-O-[cycloSaligenyl-3,5-di(tert-butyl)-6-fluoro]-3'-deoxy-3'-[$^{18}$F]fluorothymidine monophosphate 1 (Schemes 1 and 4) has all properties required of the target-specific and selective marker of the AD progression and response to therapy.

Scheme 4

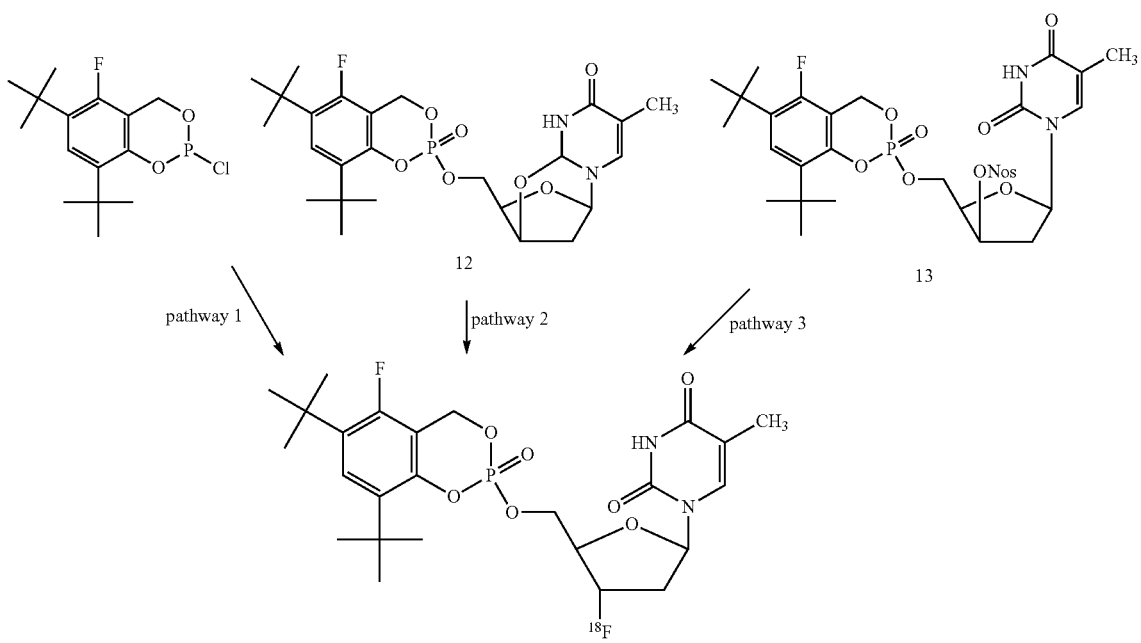

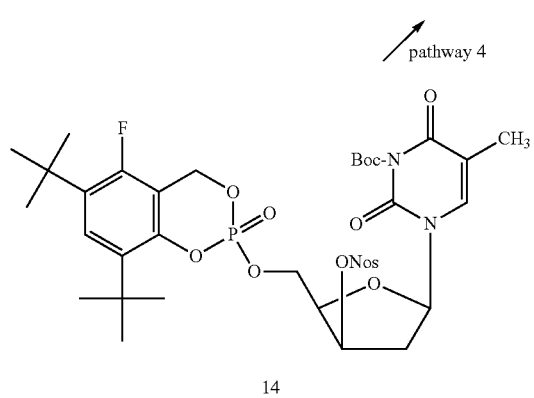

14

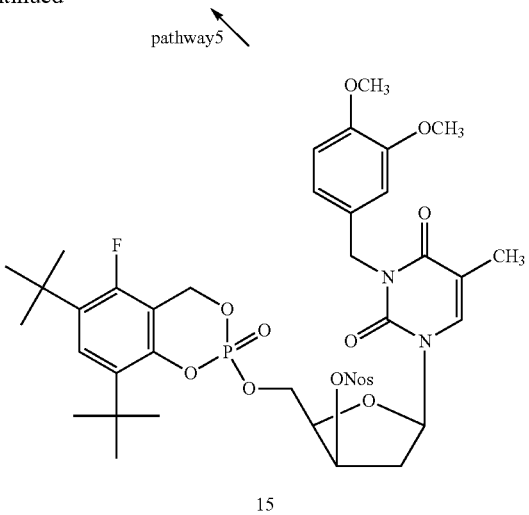

15

When planning no-carrier-added radiosyntheses of 1, several methods (Grierson et al. (2000) Nucl. Med. Biol., 27:143-156; Yun et al. (2003) J. Nucl. Med. Biol., 30:152-157; Moon et al. (2006) J. Labelled Compd. Radiopharm., 49:287-293; Wodarski et al. (2000) J. Labelled Compd. Radiopharm., 43:1211-1218; Martin et al. (2002) Nucl. Med. Biol., 29:263-273) developed for [18]FLT were assessed and radiofluorinations were found to perform better when the N3 is blocked with either alkyl or acyl groups and that such a protection appears to be crucial to obtaining higher radiochemical yields. The nosylate group at the 3'-position gives the best compromise between reactivity and stability among typically used leaving groups in the nucleophilic $^{18}$F-fluorinations. Taking into consideration the reaction conditions, stability of various intermediates as well as our ability to resolve $S_P$ (BChE-active) from $R_P$ (BChE-inactive) diastereomers, five general pathways outlined in Scheme 4 are provided which lead to the target compound 1.

Pathway 1

All starting materials and intermediates for Pathway 1 were already prepared and conditions of these reactions were optimized during the preparation of 2, 3, 4, 8 and 11 as outlined herein above. In the preparation of $^{18}$F-labeled drugs, cyclic chlorophosphites will be reacted either directly with [18]FLT, in the presence of DIPEA to yield the cyclic phosphine triester, which after the one-pot-oxidation with t-BuOOH will give a diastereomeric mixture 1. Alternatively, chlorophosphites will be first treated with DIPA to yield phosphoramidites (Tobias et al. (2001) J. Med. Chem., 44:4475-4480) followed by the coupling with [18]FLT in acetonitrile, at low temperature in the presence of pyridinium chloride, imidazolium triflate or [1]H-tetrazole as the coupling activators. Using the latter, 11 ($^{125}$I-analog of 1) has already been prepared herein with yields of ~40% and validated this direct coupling process at the non-carrier-added concentrations. This approach should give quantities of the target compound 1 sufficient for the drug characterization and identification using the non-radioactive standard 8.

Pathway 2

This approach is based on 5'-O-[cycloSaligenyl-3,5-di(tert-butyl)-6-fluoro]-2,3'-an-hydrothymidine 12 shown in Scheme 3 as the precursor for the synthesis of 1. There are two reports on the synthesis of [18]FLT starting from 2,3'-anhydro-5'-O-(4,4'-dimethoxyrityl) thymidine (Sharma et al. (2003) J. Org. Chem., 68:4574-4575; Wodarski et al. (2000) J. Labelled Compd. Radiopharm., 43:1211-1218). Under the conditions described therein, fluorination in the presence of Kryptofix 2.2.2. in DMSO at temperatures ranging from 160° C. to 175° C. yields ~6% of 18FLT. The amount of precursor and the reaction time can be optimized under the above conditions. The advantage of this method lies in the ability to resolve $S_P$ and $R_P$ 12 prior to radiofluorination affording the final product as a single diastereomer.

Pathways 3 and 4

Radiosynthesis of target compound 1 utilizes precursor 13 with 3'-O-nosyl-substituent as a good leaving group and its 3'-O-nosyl-3-N-t-Boc analogue 14. The proposed synthesis of both compounds is depicted in Scheme 5. There are several reports of successful synthesis of $^{18}$F-thymidines using similar substrates (Grierson et al. (1999) J. Labelled Comp. Radiopharm., 42:5525-5526; Griersn et al. (1997) J. Labelled Compd. Radiopharm., 40:60-62; Shields et al. (1998) Nat. Med., 4:1334-1336; Grierson et al. (2000) Nucl. Med. Biol., 27:143-156; Yun et al. (2003) J. Nucl. Med. Biol., 30:152-157; Moon et al. (2006) J. Labelled Compd. Radiopharm., 49:287-293). Yields up to 40% of [18]FLT were reported, when 3-35 mg of precursor of the type 13 or 14 were fluorinated at ~110° C. for a period of 5-15 minutes (Yun et al. (2003) J. Nucl. Med. Biol., 30:152-157). The preliminary synthesis of 2-4 herein indicates that the separation of $S_P$ and $R_P$ of 13 and 14 is achievable using HPLC. These radiosyntheses can also be evaluated in the ionic liquid as the reaction medium (Moon et al. (2006) J. Labelled Compd. Radiopharm., 49:287-293).

Scheme 5

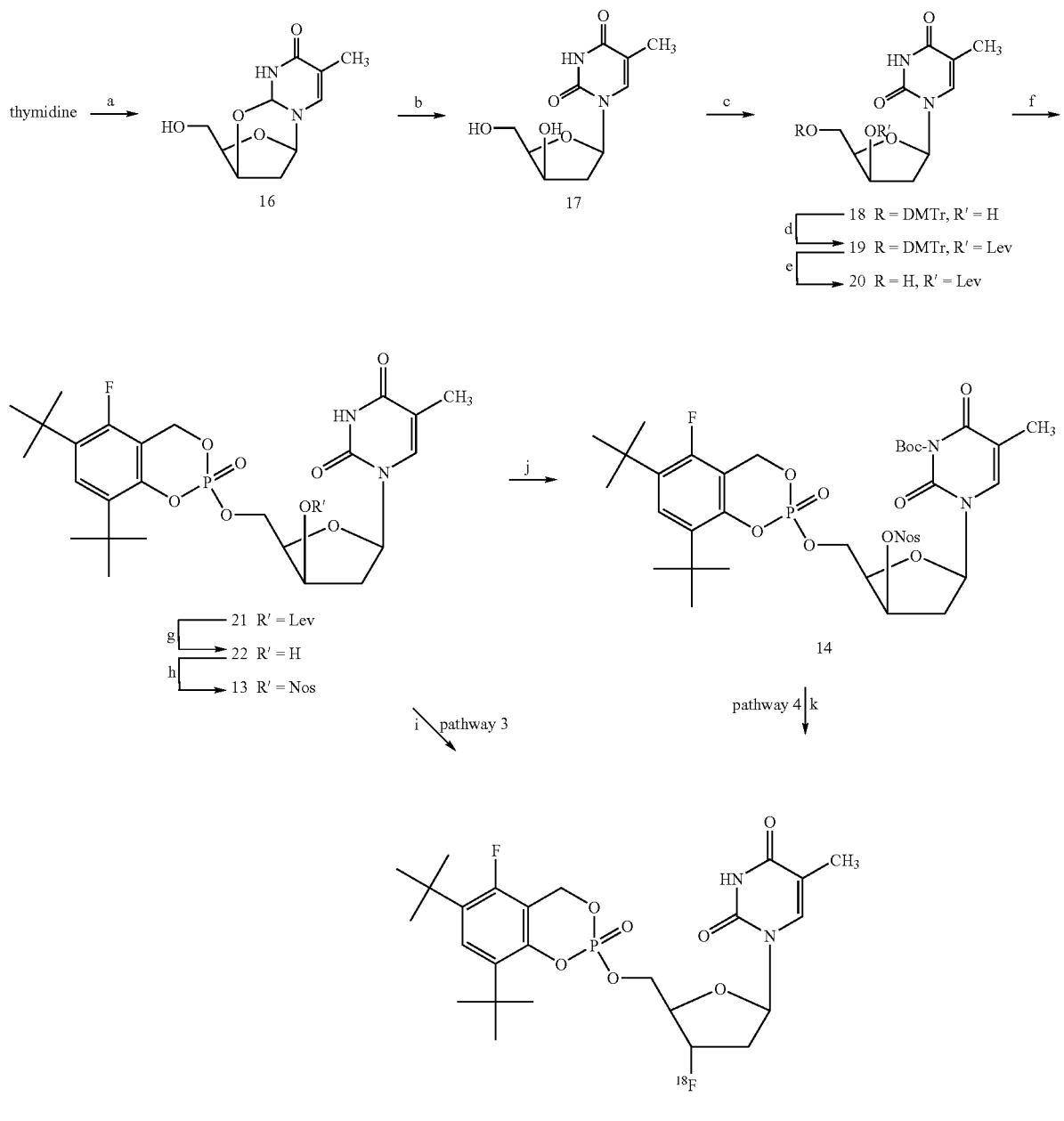

Reagents and conditions: (a) DIAD/TPP (2 equiv), CH$_3$CN, -20° C. then water; (b) LiOH (1 equiv), water then H$^+$ resin; (c) DMTrCl, pyridine; (d) levulinic acid, DCC, DMAP, THF, -40° C. ⟶ rt; (e) ZrCl$_4$, CH$_3$CN; (f) 3,5-di(tertbutyl-6-fluoro)-cycloSal chlorophosphite, DIPEA, THF, -40° C. ⟶ rt, t-BOOH, -40° C. ⟶ rt; (g) N$_2$H$_4$ × H$_2$O, pyridine/AcOH; (h) 4-NBS-Cl/AgOTf. Pyridine, 0° C.; (i) 18F, Kryptofix [2.2.2.], CH$_3$CN, 110° C.; (j) t-Boc anhydride, DMAP, THF; (k) same as in (i).

Pathway 5

As outlined in Scheme 4 this pathway features the use of cyloSal-triester 15. The approach is modeled on the 3'-O-nosyl precursor to $^{18}$FLT used in radiofluorination, which gives in the routine production of 18FLT radiochemically pure doses of >10 mCi within 100 minutes with specific activities >1 Ci/μmole at the end of synthesis. The 3-N-position is masked with N-2,4-dimethoxybenzyl group and the 3'-O-nosylate is the leaving group. The Grieson's synthesis (Grierson et al. (2000) Nucl. Med. Biol., 27:143-156) can be adopted and modified to accommodate the introduction of the 5'-O-[cycloSaligenyl-3,5-di(tert-butyl)-6-fluoro]-unit in the preparation of 15 (step g in Scheme 6).

Scheme 6

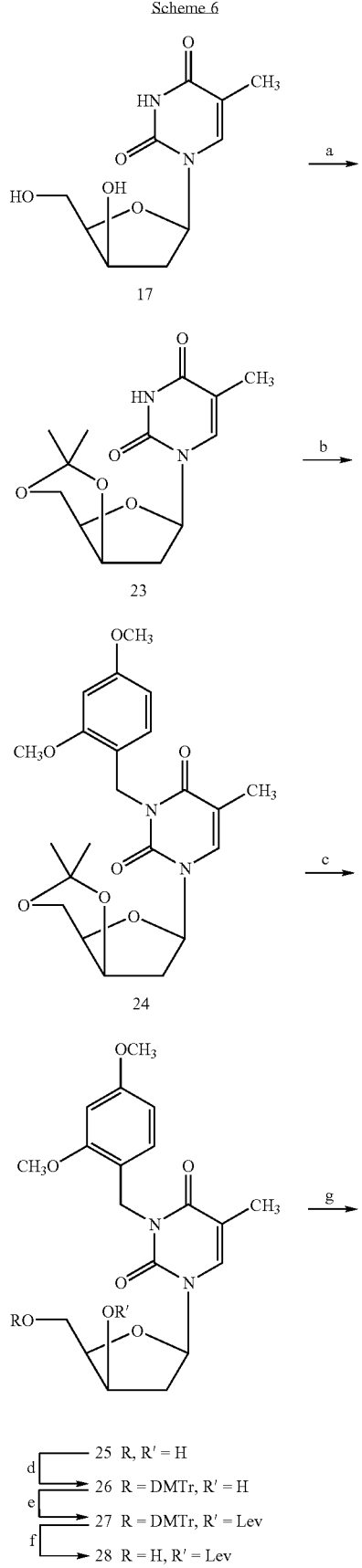

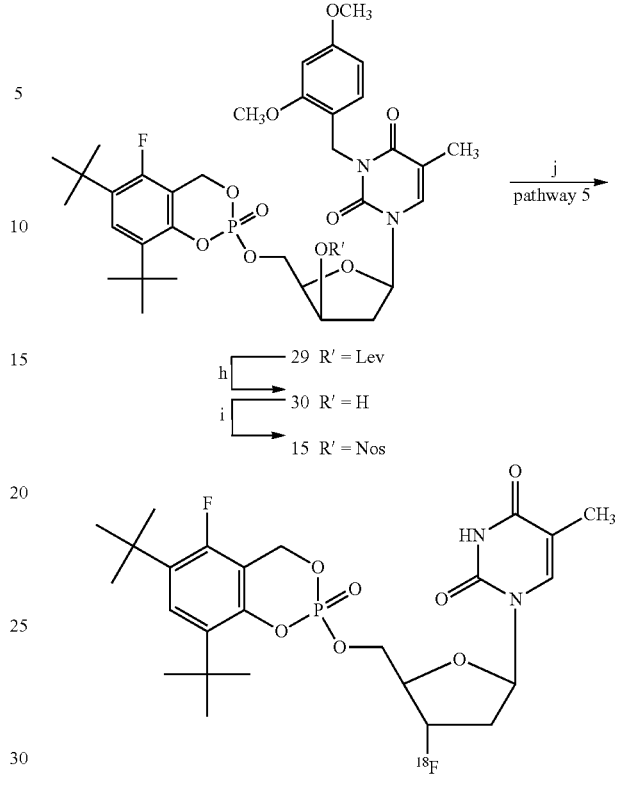

Reagents and conditions: (a) acetone/PPTS (cat), reflux; (b) 2,4-DMBn, K$_2$CO$_3$/MEK, reflux, phase transfer catalyst; (c) EtOH/water, PPTS (cat), reflux; (d) DMTr-Cl, pyridine, rt; (e) levulinic acid, DCC, DMAP (cat), rt; (f) ZrCl$_4$ (1 equiv), CH$_3$CN, 5 minutes; (g) 3,5-di(tertbutyl-6-fluoro)-cycloSalchlorophosphite, DIPEA, CH$_3$CN, -40° C. ⟶ rt, t-BOOH, -40° C. ⟶ rt;
(h) N$_2$H$_4$ × H$_2$O, pyridine/AcOH, rt, 5 minutes; (i) 4-NBS-Cl/AgOTF, pyridine, 0° C.; (j) $^{18}$F, K$_2$CO$_3$, Kryptofix 2.2.2., CH$_3$CN, 100° C., 10 minutes then CAN, CH$_3$CN/EtOH/water (4:1:1), 100° C., 3 minutes.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

Several publications and patent documents are cited throughout the specification in order to describe the state of the art to which this invention pertains. Each of these citations is incorporated herein by reference as though set forth in full.

What is claimed is:
1. A compound of the formula:

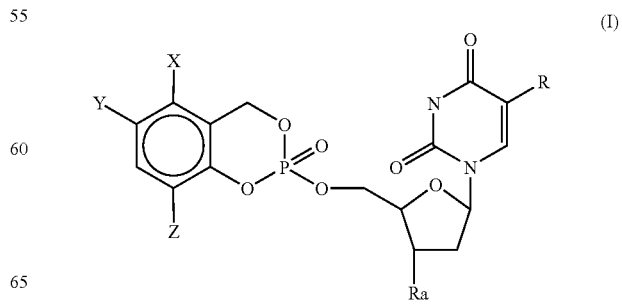

wherein R represents a substituted or unsubstituted, straight or branched chain, saturated or unsaturated hydrocarbyl ($C_1$-$C_{15}$) group, radioactive halogen, non-radioactive halogen;

$R_a$ represents radioactive halogen, non-radioactive halogen, hydroxyl, one of R and Ra being radioactive halogen;

X represents hydrogen, non-radioactive halogen, radioactive halogen;

Y represents hydrogen, a straight or branched chain, substituted or unsubstituted, saturated or unsaturated hydrocarbyl ($C_1$-$C_4$) group, and $^{11}$C-containing analogues of said hydrocarbyl group; and Z represents hydrogen, straight or branched chain, substituted or unsubstituted saturated or unsaturated hydrocarbyl ($C_1$-$C_4$) group, and $^{11}$C-containing analogues of said hydrocarbyl group.

2. The compound of claim 1, wherein R represents straight chain alkyl ($C_1$-$C_8$) or aryl; $R_a$ represents $^{18}$F; X represents F; Y represents branched chain alkyl ($C_1$-$C_4$); Z represents branched chain alkyl ($C_1$-$C_4$).

3. The compound 5'-O-[cycloSaligenyl-3,5-di(tert-butyl)-6-fluoro]-3'-[$^{18}$F]fluoro thymidine monophosphate, according to claim 1.

4. The compound 5'-O-[cycloSaligenyl-3,5-di(tert-butyl)-6-fluoro-2',3'-deoxy-3'-fluoro-5-[$^{125}$I]iodouridine monophosphate, according to claim 1.

5. A method for making an ante mortem diagnosis of Alzheimer's disease comprising:
 a. administering to a patient suspected of having Alzheimer's disease a compound according to claim 1 in an amount of up to 20 mCi (up to 740 MBq) effective to bind to butyrylcholinesterase (BChE) present in the brain of said patient; and
 b. detecting the amount of BChE bound by said compound.

6. The method of claim 5, further comprising comparing the amount of BChE detected to a positive or negative control.

7. The method of claim 5, wherein said detecting is carried out by imaging.

8. The method of claim 7, wherein the imaging is positron emission tomography (PET) or single photon emission computed tomography (SPECT).

9. The method of claim 5, wherein said compound is administered intravenously or intracarotid.

10. The method according to claim 6, wherein steps (a) and (b) are repeated at least once after passage of a predetermined time interval, an increase in said radioactive drug uptake during said time interval being indicative of the progression of AD in said patient.

11. The method according to claim 6, wherein steps (a) and (b) are repeated at least once after passage of a predetermined time interval during which AD therapy is administered to said patient, a decrease in said radioactive drug uptake being indicative of the effectiveness of said therapy.

* * * * *